(12) United States Patent
Lei et al.

(10) Patent No.: US 9,403,811 B2
(45) Date of Patent: Aug. 2, 2016

(54) CRYSTALLINE FORMS OF AZILSARTAN MEDOXOMIL POTASSIUM AND PREPARATION AND USES THEREOF

(71) Applicants: SUNSHINE LAKE PHARMA CO., LTD., Dongguan, Guangdong (CN); RUYUAN HEC PHARM CO., LTD., Guangdong (CN)

(72) Inventors: Xin Lei, Dongguan (CN); Zhiqing Lv, Dongguan (CN); Tianming Wang, Dongguan (CN)

(73) Assignees: SUNSHINE LAKE PHARMA CO., LTD., Dongguan, Guangdong (CN); RUYUAN HEC PHARM CO., LTD., Rucheng Town, Guangdong (CN)

( * ) Notice: Subject to any disclaimer, the term of this patent is extended or adjusted under 35 U.S.C. 154(b) by 25 days.

(21) Appl. No.: 14/371,737

(22) PCT Filed: Jan. 14, 2013

(86) PCT No.: PCT/CN2013/070427
§ 371 (c)(1),
(2) Date: Jul. 11, 2014

(87) PCT Pub. No.: WO2013/104342
PCT Pub. Date: Jul. 18, 2013

(65) Prior Publication Data
US 2014/0364464 A1    Dec. 11, 2014

(30) Foreign Application Priority Data

Jan. 14, 2012  (CN) .......................... 2012 1 0010823

(51) Int. Cl.
*C07D 413/14*    (2006.01)
(52) U.S. Cl.
CPC .................................... *C07D 413/14* (2013.01)
(58) Field of Classification Search
CPC .................................................... C07D 271/06
See application file for complete search history.

(56) References Cited

U.S. PATENT DOCUMENTS

2005/0187269 A1    8/2005  Kuroita et al.

FOREIGN PATENT DOCUMENTS

| CN | 102351853 A | | 2/2012 |
|---|---|---|---|
| WO | 2012090043 A1 | | 7/2012 |
| WO | 2013088384 A2 | | 6/2013 |
| WO | 2013124748 A1 | | 8/2013 |
| WO | WO2013124748 | * | 8/2013 |
| WO | WO2014020381 | * | 2/2014 |

OTHER PUBLICATIONS

Polymorphism in Pharmaceutical Solids, edited by Brittain, 1999, Marcel Dekker Inc., p. 228-229, 236.*
ISR, Apr. 2013.
Written Opinion, Apr. 2013.

* cited by examiner

*Primary Examiner* — Rebecca Anderson
*Assistant Examiner* — Karen Cheng
(74) *Attorney, Agent, or Firm* — Kam W. Law; Squire Patton Boggs (US) LLP

(57) ABSTRACT

The present invention relates to the field of pharmaceutical chemistry. Disclosed herein is a crystalline form of azilsartan medoxomil potassium, which is substantially pure. The crystalline form is crystalline form A, form B, form C, form D, form E, form F, form G, form H, form I, form J, form K or form L. The substantially pure crystalline forms of azilsartan medoxomil potassium of the invention generally have good properties such as high solubility, high bioavailability, good stability, long shelf life and good antistatic property. The crystalline forms of azilsartan medoxomil potassium generally exhibit an excellent performance in reducing clinical systolic blood pressure (SBP) and average 24-hour SBP. Disclosed herein are methods of preparing the substantially pure crystalline forms of azilsartan medoxomil potassium, pharmaceutical compositions comprising the crystalline forms, and preparation methods and uses thereof.

14 Claims, 6 Drawing Sheets

CRYSTALLINE FORMS OF AZILSARTAN MEDOXOMIL POTASSIUM AND PREPARATION AND USES THEREOF

CROSS-REFERENCE TO RELATED APPLICATIONS

This is a U.S. national stage application of the International Patent Application No. PCT/CN2013/070427, filed on Jan. 14, 2013, which claims priority to Chinese Patent Application No. CN 201210010823.3, filed on Jan. 14, 2012, all of which are incorporated herein by reference in their entirety.

FIELD OF THE INVENTION

The present invention relates to the field of pharmaceutical chemistry. More particularly, the invention relates to novel crystalline forms of azilsartan medoxomil potassium, pharmaceutical compositions comprising the crystalline forms, and preparation methods and uses thereof.

BACKGROUND OF THE INVENTION

Azilsartan medoxomil, also know as (5-methyl-2-oxo-1,3-dioxol-4-yl)methyl 2-ethoxy-1-([2'-(5-oxo-4,5-dihydro-1,2,4-oxadiazol-3-yl)biphenyl-4-yl]methyl)-1H-20 benzimidazole-7-carboxylate, having formula (I), is an angiotensin II antagonist prodrug of azilsartan (TAK-536), for the once-daily oral treatment of hypertension in adults, either alone or in combination with other antihypertensive agents,

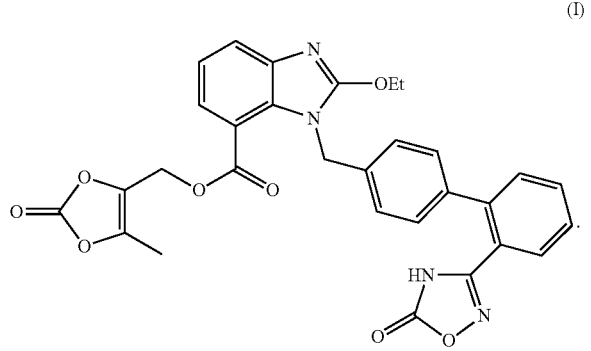 [SMILES: CCOc1nc2cccc(C(=O)OCc3oc(=O)oc3C)c2n1Cc1ccc(-c2ccccc2-c2noc(=O)[nH]2)cc1]

(I)

Azilsartan medoxomil potassium salt has formula (II):

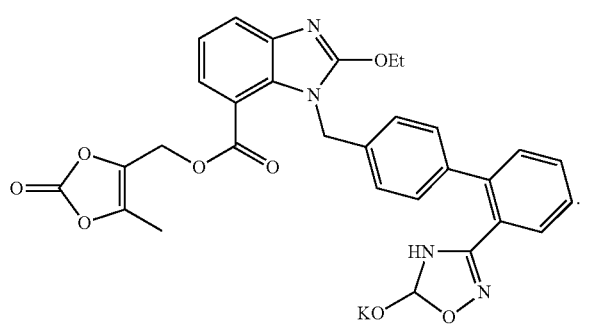

(II)

Azilsartan medoxomil potassium was first disclosed by Takeda in U.S. Pat. No. 7,157,584, the method of preparation of azilsartan medoxomil potassium is disclosed in the specification of U.S. Pat. No. 7,157,584, (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate was dissolved in acetone, a solution of potassium 2-ethylhexanoate in acetone was added. The mixture was left standing overnight in a refrigerator, and the precipitated crystals were collected by filtration and dried under reduced pressure at room temperature to give azilsartan medoxomil potassium with a melting point of 196° C.

However, U.S. Pat. No. 7,157,584 do not fully characterize the azilsartan medoxomil potassium polymorphs. Therefore, we do not know the polymorphic forms of the azilsartan medoxomil potassium disclosed in this reference.

A drug such as azilsartan medoxomil potassium may exist in different crystalline forms, which may have significant differences from each other in appearances, solubilities, melting points, dissolution rates, bioavailabilities, stability, efficacy and the like. Therefore, there is a need for novel crystalline forms of azilsartan medoxomil potassium having better physicochemical properties, especially, relatively higher solubilities, bioavailabilities and/or efficacies. There is also a constant need for a low cost and industrial friendly process for preparing the crystalline forms of azilsartan medoxomil potassium.

SUMMARY OF THE INVENTION

Provided here is a crystalline form of azilsartan medoxomil potassium, wherein the crystalline form is form A, form B, form C, form D, form E, form F, form G, form H, form I, form J, form K or form L and wherein:

a) form A has an X-ray powder diffraction pattern comprising a peak at about 7.41, 10.74, 18.19, 22.83, 23.29, 23.66 and 24.80 degrees in term of two theta;

b) form B has an X-ray powder diffraction pattern comprising one or more peaks at about 23.01, 23.11, 26.01, 28.32 degrees in term of two theta;

c) form C has an X-ray powder diffraction pattern comprising one or more peaks at about 6.20, 18.70 degrees in term of two theta;

d) form D has an X-ray powder diffraction pattern comprising one or more peaks at about 6.18, 15.22, 18.62, 19.34, 23.54, 24.88, 26.94 degrees in term of two theta;

e) form E has an X-ray powder diffraction pattern comprising one or more peaks at about 6.16, 13.34, 16.22, 18.58, 19.88, 21.46, 22.86, 26.84, 28.28, 33.62 degrees in term of two theta;

f) form F has an X-ray powder diffraction pattern comprising one or more peaks at about 17.96, 22.52, 23.32 degrees in term of two theta;

g) form G has an X-ray powder diffraction pattern comprising one or more peaks at about 6.18, 13.32, 14.10, 14.44, 16.02, 17.80, 18.70, 21.30, 22.70, 22.90, 23.70, 24.38, 24.74, 26.90, 28.28, 40.50 degrees in term of two theta;

h) form H has an X-ray powder diffraction pattern comprising one or more peaks at about 6.18, 13.32, 14.10, 14.36, 17.34, 18.72, 22.80, 23.56, 27.02 degrees in term of two theta;

i) form I has an X-ray powder diffraction pattern comprising one or more peaks at about 6.06, 12.10, 13.86, 15.00, 18.72, 19.54, 21.54, 23.04, 23.88, 25.44, 28.36 degrees in term of two theta;

j) form J has an X-ray powder diffraction pattern comprising one or more peaks at about 13.18, 15.90, 20.18, 21.10, 22.22, 22.52, 23.24, 23.98 degrees in term of two theta;

k) form K has an X-ray powder diffraction pattern comprising one or more peaks at about 6.06, 12.48, 13.22, 13.92, 14.34, 14.62, 15.84, 18.60, 20.14, 20.92, 22.66, 23.66, 24.00, 26.86 degrees in term of two theta; or l) form L has an X-ray powder diffraction pattern comprising one or more peaks at about 10.34, 18.26, 20.92, 22.10, 24.06 degrees in term of two theta.

Figure 3:
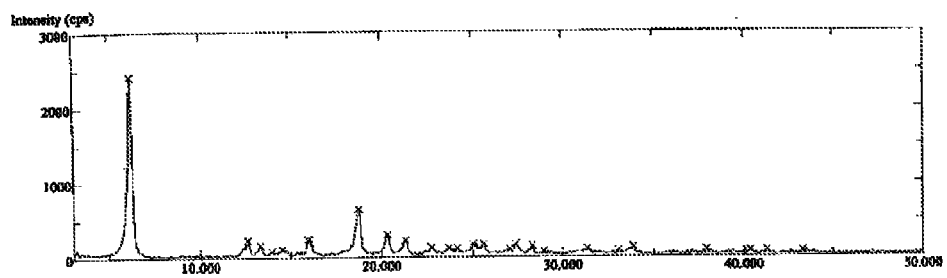
FIG. 3 depicts the X-ray powder diffractogram of the crystalline form C of azilsartan medoxomil potassium.

In some embodiments, form C has an X-ray powder diffraction pattern comprising one or more peaks at about 6.20, 12.64, 13.36, 14.48, 16.00, 18.70, 20.30, 21.38, 22.78, 23.80, 25.04 degrees in term of two theta; or an X-ray powder diffraction pattern comprising one or more peaks at about 6.20, 12.64, 13.36, 14.02, 14.48, 16.00, 17.74, 18.12, 18.70, 20.30, 21.38, 22.78, 23.80, 25.04, 25.60, 27.52, 28.16, 28.32, 31.32 degrees in term of two theta; or an X-ray powder diffraction pattern substantially as depicted in FIG. 3 wherein the peak at about 6.20 degree in term of two theta has a relative intensity of at least about 50%, at least about 60%, at least about 70%, at least about 80%, at least about 90% or at least about 99% with respect to the strongest peak in the X-ray powder diffraction pattern.

Figure 5:
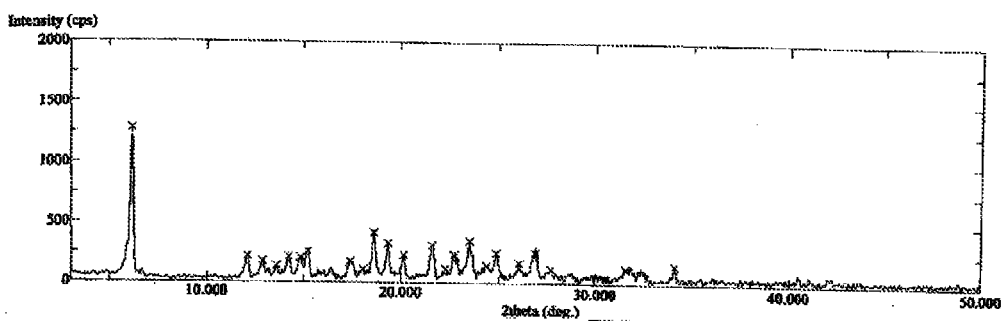
FIG. 5 depicts the X-ray powder diffractogram of the crystalline form D of azilsartan medoxomil potassium.

In some embodiments, form D has an X-ray powder diffraction pattern comprising one or more peaks at about 6.18, 12.14, 12.90, 14.26, 14.84, 15.22, 18.62, 19.34, 20.16, 21.62, 23.54, 24.88, 26.94 degrees in term of two theta; or an X-ray powder diffraction pattern comprising one or more peaks at about 6.18, 12.14, 12.90, 13.64, 14.26, 14.84, 15.22, 17.38, 18.04, 18.62, 19.34, 20.16, 21.62, 22.30, 22.76, 23.54, 24.40, 24.88, 26.08, 26.94, 27.74, 31.56, 34.06 degrees in term of two theta; or an X-ray powder diffraction pattern substantially as depicted in FIG. 5 wherein the peak at about 6.18 degree in term of two theta has a relative intensity of at least about 50%, at least about 60%, at least about 70%, at least about 80%, at least about 90% or at least about 99% with respect to the strongest peak in the X-ray powder diffraction pattern.

Figure 9:
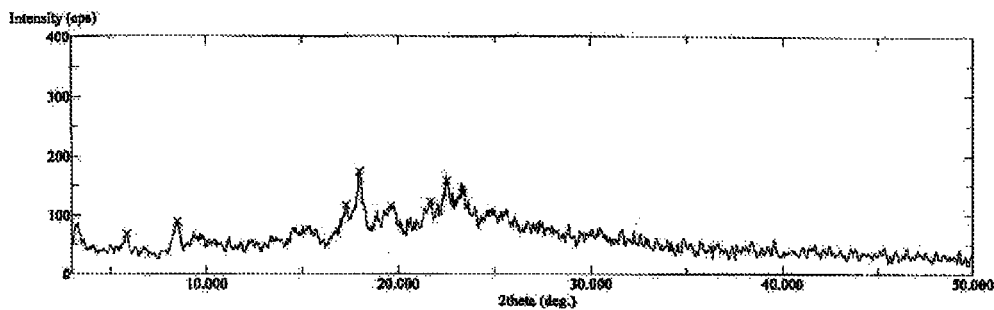
FIG. 9 depicts the X-ray powder diffractogram of the crystalline form F of azilsartan medoxomil potassium.

In some embodiments, form F has an X-ray powder diffraction pattern comprising one or more peaks at about 5.90, 8.46, 17.26, 17.96, 19.60, 21.66, 22.52, 23.32 degrees in term of two theta; or an X-ray powder diffraction pattern substantially as depicted in FIG. 9.

Figure 12:
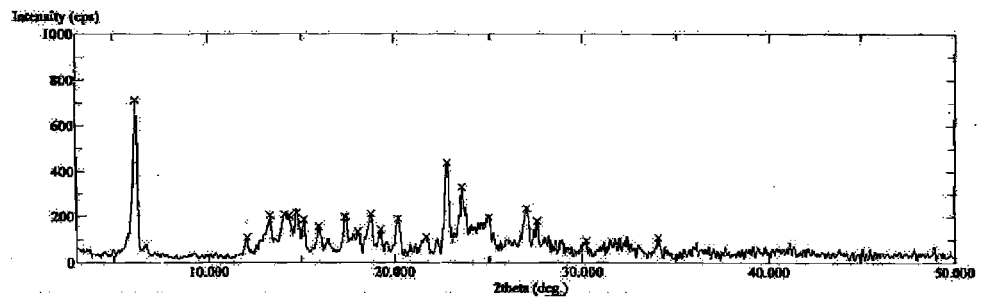
FIG. 12 depicts the X-ray powder diffractogram of the crystalline form H of azilsartan medoxomil potassium.

In some embodiments, form H has an X-ray powder diffraction pattern comprising one or more peaks at about 6.18, 12.08, 13.32, 14.10, 14.36, 15.14, 15.92, 17.34, 18.02, 18.72, 19.24, 20.18, 21.68, 22.80, 23.56, 24.96, 27.02, 27.60, 30.2 degrees in term of two theta; or an X-ray powder diffraction pattern substantially as depicted in FIG. 12 wherein the peak at about 6.18 degree in term of two theta has a relative intensity of at least about 50%, at least about 60%, at least about 70%, at least about 80%, at least about 90% or at least about 99% with respect to the strongest peak in the X-ray powder diffraction pattern.

Figure 14:
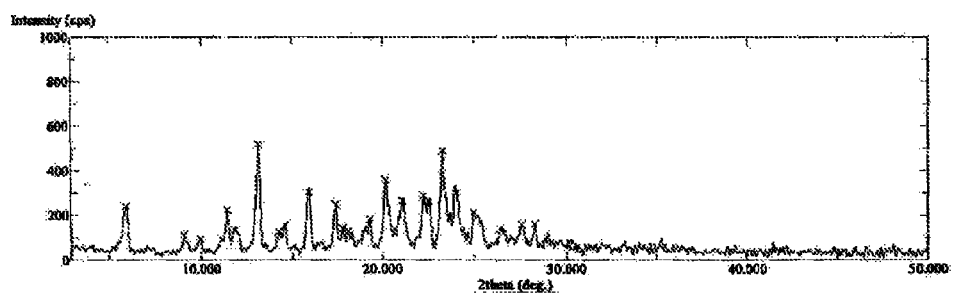
FIG. 14 depicts the X-ray powder diffractogram of the crystalline form J of azilsartan medoxomil potassium.

In some embodiments, form J has an X-ray powder diffraction pattern comprising one or more peaks at about 5.94, 9.04, 9.94, 11.46, 11.88, 13.18, 14.26, 14.58, 15.90, 17.38, 17.80, 18.10, 19.32, 20.18, 21.10, 22.22, 22.52, 23.24, 23.98, 24.96, 26.44, 27.60, 28.30 degrees in term of two theta; or an X-ray powder diffraction pattern substantially as depicted in FIG. 14 wherein the peak at about 13.18 degree in term of two theta has a relative intensity of at least about 50%, at least about 60%, at least about 70%, at least about 80%, at least about 90% or at least about 99% with respect to the strongest peak in the X-ray powder diffraction pattern.

Figure 16:
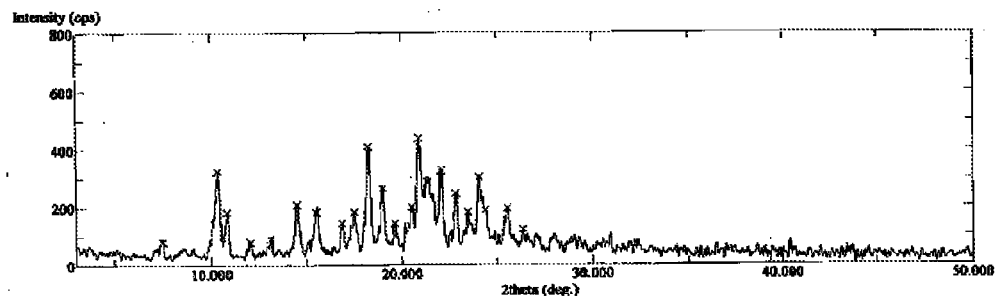
FIG. 16 depicts the X-ray powder diffractogram of the crystalline form L of azilsartan medoxomil potassium.

In some embodiments, form L has an X-ray powder diffraction pattern comprising one or more peaks at about 10.34, 10.82, 14.52, 15.52, 17.52, 18.26, 19.00, 20.54, 20.92, 21.38, 22.10, 22.84, 23.48, 24.06, 24.36, 25.56 degrees in term of two theta; or an X-ray powder diffraction pattern comprising one or more peaks at about 7.48, 10.34, 10.82, 12.04, 13.10, 14.52, 15.52, 16.88, 17.52, 18.26, 19.00, 19.62, 20.54, 20.92, 21.38, 22.10, 22.84, 23.48, 24.06, 24.36, 25.56, 26.36 degrees in term of two theta; or an X-ray powder diffraction pattern substantially as depicted in FIG. 16 wherein the peak at about 20.92 degree in term of two theta has a relative intensity of at least about 50%, at least about 60%, at least about 70%, at least about 80%, at least about 90% or at least about 99% with respect to the strongest peak in the X-ray powder diffraction pattern.

Also provided herein is a process for preparing the crystalline form of azilsartan medoxomil potassium, comprising dissolving azilsartan medoxomil in a solvent to form a solution; to the solution was added potassium salt, then forming crystals at a suitable temperature, wherein the solvent is one or more polar solvents, one or more non-polar solvents or a combination thereof, wherein the solvent is selected from dimethyl formamide, dimethyl sulfoxide, N-methyl-2-pyrrolidone, water, ether solvents, ketone solvents, ester solvents, aromatic hydrocarbon solvents, alkane solvents, nitrile solvents and combinations thereof In some embodiments, wherein the potassium salt is organic acid potassium salt or inorganic acid salt, comprising potassium nitrate, potassium sulfate, potassium sulfite, potassium bromate, potassium bicarbonate, potassium thiocyanate, dipotassium hydrogen phosphate, potassium dihydrogen phosphate, potassium hydrogen phthalate, potassium acetate, Potassium formate, Potassium di-tert-butylphosphate, dipotassium glycyrrhizinate, Potassium 2-ethylhexanoate, potassium ethyl xanthate, potassium sorbate and combination thereof.

In some embodiments, wherein the ether solvents are selected from methyl-tetrahydrofuran, tetrahydrofuran, dioxane, ethylene glycol dimethyl ether, or methyl tert-butyl ether; wherein the ketone solvents are selected from acetone, methyl ethyl ketone, or 4-methyl-2-pentanone; wherein the ester solvents are selected from ethyl acetate, isopropyl acetate, n-butyl acetate, tert-butyl acetate, sec-butyl acetate, wherein the alkane solvents are selected from dichloromethane, 1,2-dichloroethane, chloroform, carbon tetrachloride, nitroethane, n-hexane, cyclohexane or n-pentane or n-heptane; wherein aromatic hydrocarbon solvents are selected from benzene, toluene or xylene; wherein nitrile solvents are selected from acetonitrile or malononitrile.

Also provided herein is a process for preparing the crystalline form of azilsartan medoxomil potassium, comprising dissolving azilsartan medoxomil potassium in a solvent, then crystallization from the solvent, wherein the solvent is one or more polar solvents, one or more non-polar solvents or a combination thereof, wherein the solvent is selected from dimethyl formamide, dimethyl sulfoxide, N-methyl-2-pyrrolidone, water, ether solvents, ketone solvents, ester solvents, aromatic hydrocarbon solvents, alkane solvents, nitrile solvents and combinations thereof In some embodiments, wherein the ether solvents are selected from methyl-tetrahydrofuran, tetrahydrofuran, dioxane, ethylene glycol dimethyl ether, or methyl tert-butyl ether; wherein the ketone solvents are selected from acetone, methyl ethyl ketone, or 4-methyl-2-pentanone; wherein the ester solvents are selected from ethyl acetate, isopropyl acetate, n-butyl acetate, tert-butyl acetate, sec-butyl acetate, wherein the alkane solvents are selected from dichloromethane, 1,2-dichloroethane, chloroform, carbon tetrachloride, nitroethane, n-hexane, cyclohexane or n-pentane or n-heptane; wherein aromatic hydrocarbon solvents are selected from benzene, toluene or xylene; wherein nitrile solvents are selected from acetonitrile or malononitrile.

In some embodiments, the process for preparing crystalline form C of azilsartan medoxomil potassium in substantially pure, wherein the solvent is selected from propanone, 4-methyl-2-pentanone, ethyl acetate, dichloromethane, dichloroethane, isobutyl acetate, sec-butyl acetate, methyl tetrahydrofuran, nitroethane, 1,2-dichloroethane, methyl ethyl ketone, dioxane, ethylene glycol dimethyl ether, acetonitrile, tetrahydrofuran, cyclohexane and combinations thereof.

Also provided herein is a pharmaceutical composition comprising the crystalline form of azilsartan medoxomil potassium and one or more of inert excipients or carriers.

In some embodiments, wherein the crystalline form of azilsartan medoxomil potassium is form A, form B, form C, form D, form E, form F, form G, form H, form I, form J, form K or form L and wherein the crystalline form of azilsartan medoxomil potassium is substantially pure.

Also provided herein is method of preventing or treating hypertension in a patient by administering to the patient a pharmaceutically effective amount of the crystalline forms A-L of azilsartan medoxomil potassium.

DETAILED DESCRIPTION OF THE INVENTION

Definitions and General Terminology

As used herein, the term "crystalline form" of a compound refers to a unique ordered arrangement and/or conformations of molecules in the crystal lattice of the compound.

As used herein, a crystalline form that is "substantially pure" refers to a crystalline form that is substantially free of one or more other crystalline forms, i.e., the crystalline form has a purity of at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form has less than 20%, less than 10%, less than 5%, less than 3%, less than 1%, less than 0.5%, less than 0.1%, or less than 0.01% of the one or more other crystalline forms, based on the total volume or weight of the crystalline form and the one or more other crystalline form.

As used herein, a crystalline form that is "substantially free" of one or more other crystalline forms refers to a crystalline form containing less than 20%, less than 10%, less than 5%, less than 4%, less than 3%, less than 2%, less than 1%, less than 0.5%, less than 0.1%, or less than 0.01% of the one or more other crystalline form, based on the total volume or weight of the crystalline form and the one or more other crystalline form.

As used herein, an X-ray powder diffraction pattern that is "substantially as depicted" in a figure refers to an X-ray powder diffraction pattern having at least 50%, at least 60%, at least 70%, at least 80%, at least 90%, at least 95%, or at least 99% of the peaks shown in the figure.

As used herein, the term "relative intensity" refers to the intensity of a peak with respect to the intensity of the strongest peak in the X-ray powder diffraction (XRPD) pattern which is regarded as 100%.

As used herein, the term "anti-solvent" refers to a solvent which can promote supersaturation and/or crystallization. In some embodiments, the solubility of azilsartan medoxomil potassium in the anti-solvent is less than 0.001 g/L, less than 0.01 g/L, less than 0.1 g/L, less than 0.2 g/L, less than 0.3 g/L, less than 0.4 g/L, less than 0.5 g/L, less than 0.6 g/L, less than 0.8 g/L, less than 1 g/L, less than 2 g/L, less than 3 g/L, less than 4 g/L, less than 5 g/L, less than 6 g/L, less than 7 g/L, less than 8 g/L, less than 9 g/L, or less than 10 g/L of the anti-solvent.

As used herein, the term "room temperature" refers to a temperature from about 18° C. to about 30° C. or a temperature from about 20° C. to about 24° C. or a temperature at about 22° C.

As used herein, when referring to a spectrum and/or to data presented in a graph, the term "peak" refers to a feature that one skilled in the art would recognize as not attributable to background noise.

In the following description, all numbers disclosed herein are approximate values, regardless whether the word "about" is used in connection therewith. The value of each number may differ by 1%, 2%, 5%, 7%, 8%, 10%, 15% or 20%. Therefore, whenever a number having a value N is disclosed, any number having the value N+/−1%, N+/−2%, N+/−3%, N+/−5%, N+/−7%, N+/−8%, N+/−10%, N+/−15% or 20 N+/−20% is specifically disclosed, wherein "+/−" refers to plus or minus. Whenever a numerical range with a lower limit, RL, and an upper limit, RU, is disclosed, any number falling within the range is specifically disclosed. In particular, the following numbers within the range are specifically disclosed: R=RL+k*(RU−RL), wherein k is a variable ranging from 1% to 100% with a 1% increment, i.e., k is 1%, 2%, 3%, 4%, 5%, . . . , 50%, 51%, 52%, . . . , 95%, 96%, 97%, 98%, 99%, or 100%. Moreover, any numerical range defined by two R numbers as defined above is also specifically disclosed.

The present invention provides a novel crystalline form of azilsartan medoxomil potassium and its preparation thereof.

Provided herein are novel crystalline forms of azilsartan medoxomil potassium. The crystalline forms of a drug compound may have different chemical and physical properties, including melting point, chemical reactivity, apparent solubility, dissolution rate, optical and mechanical properties, vapor pressure and density. These properties can have a direct effect on the ability to process and/or manufacture the drug compound and the drug product, as well as on drug product stability, dissolution, and bioavailability. Thus the crystalline forms of azilsartan medoxomil potassium can affect the quality, safety, and efficacy of a drug product comprising azilsartan medoxomil potassium.

The principal embodiment of the present invention is to investigate whether azilsartan medoxomil potassium can exist in crystalline form. Unexpectedly, we have found that azilsartan medoxomil potassium can exist in many novel crystalline forms including form A, form B, form C, form D, form E, form F, form G, form H, form I, form J, form K, form L. In some embodiments, each of the novel crystalline form of azilsartan medoxomil potassium is substantially pure.

The crystalline forms of azilsartan medoxomil potassium may exhibit increased solubility and thermal stability; may provide better oral bioavailability and/or a better dissolution profile for a particular formulation; may also provide free-flowing easily filterable, and/or thermally stable characteristics that are suitable for use in particular formulations. The crystalline forms of azilsartan medoxomil potassium have low electrostatic property which is convenient to the operation of the production process. The crystalline forms of azilsartan medoxomil potassium may exhibit reducing clinical systolic blood pressure (SBP) and have a good performance in term of the 24-hour average clinical systolic. Therefore, they are suitable for preparing pharmaceutical compositions for the prevention and/or treatment of hypertension.

Figure 1:
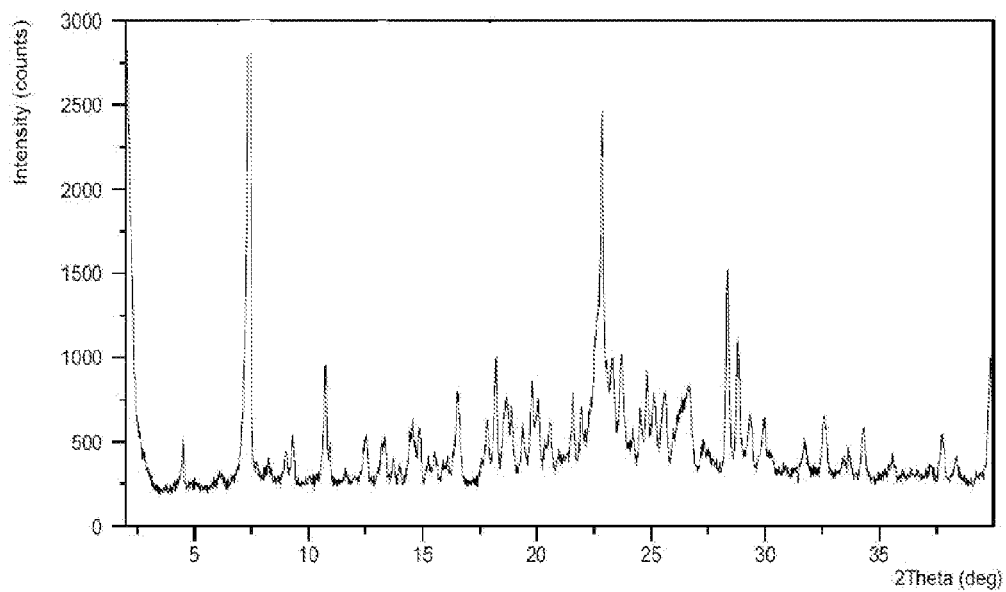
FIG. 1 depicts the X-ray powder diffractogram of the crystalline form A of azilsartan medoxomil potassium.

In some embodiments, the crystalline form of azilsartan medoxomil potassium is crystalline form A. In certain embodiments, form A of azilsartan medoxomil potassium disclosed herein is substantially pure. In some embodiments, form A has an X-ray powder diffraction pattern (XRPD) comprising a peak at about 7.41 degree in term of two theta; In certain embodiments, form A has an X-ray powder diffraction pattern comprising one or more peaks at about 7.41, 22.83 degrees in term of two theta; In some embodiments, form A has an X-ray powder diffraction pattern comprising one or more peaks at about 7.41, 10.74, 18.19, 22.83, 23.29, 23.66 and 24.8 degrees in term of two theta; In certain embodiments, form A has an X-ray powder diffraction pattern comprising one or more peaks at about 4.50, 7.41, 8.97, 9.29, 10.74, 10.91, 12.54, 13.74, 14.55, 14.87, 15.52, 15.98, 16.49, 17.80, 18.19, 18.66, 18.90, 19.38, 19.74, 20.03, 20.57, 21.55, 21.91, 22.83, 23.29, 23.67, 24.20, 24.50, 24.80, 25.11, 25.63, 26.68, 27.30, 28.32, 28.77, 29.34, 29.95, 31.71 and 32.54 degrees in term of two theta; In certain embodiments, form A has an X-ray powder diffraction pattern substantially as depicted in FIG. 1 wherein the peak at about 7.41 degree in term of two theta has a relative intensity of at least about 50%, at least about 60%, at least about 70%, at least about 80%, at least about 90% or at least about 99% with respect to the strongest peak in the X-ray powder diffraction pattern.

In certain embodiments, the characteristics of form A can be detected, identified, classified and characterized using well-known techniques such as, but not limited to infrared (IR) spectroscopy, differential scanning calorimetry (DSC), form A melts at about 215.8° C. to about 222.4° C. by DSC analysis.

Figure 2:
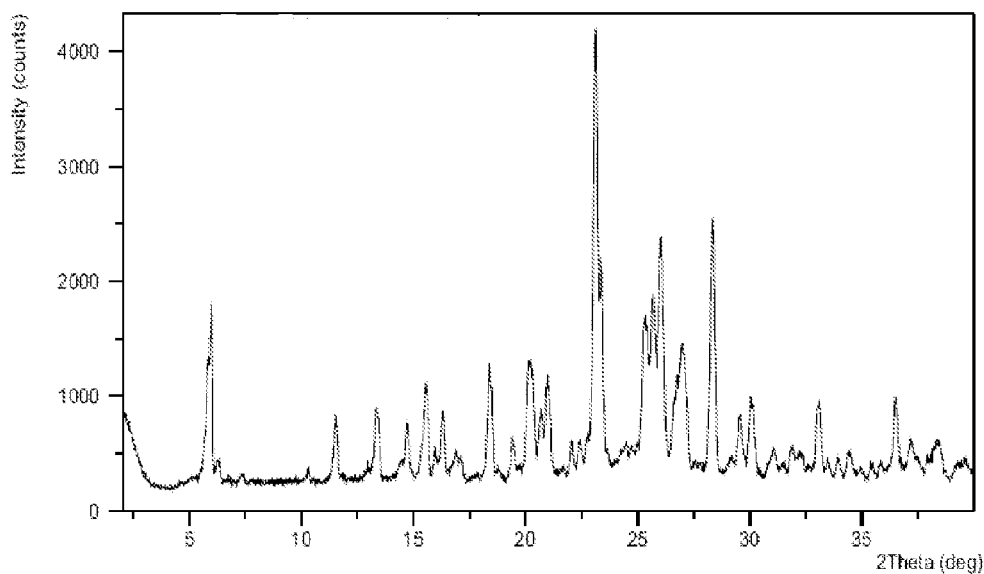
FIG. 2 depicts the X-ray powder diffractogram of the crystalline form B of azilsartan medoxomil potassium.

In some embodiments, the crystalline form of azilsartan medoxomil potassium is crystalline form B. In certain embodiments, form B of azilsartan medoxomil potassium disclosed herein is substantially pure. In some embodiments, form B has an X-ray powder diffraction pattern (XRPD) comprising a peak at about 23.11 degree in term of two theta; In certain embodiment, form B has an X-ray powder diffraction pattern comprising one or more peaks at about 23.01, 23.11, 26.01, 28.32 degrees in term of two theta; In some embodiments, form B has an X-ray powder diffraction pattern comprising one or more peaks at about 5.79, 5.99, 15.56, 18.36, 20.07, 20.30, 20.93, 23.01, 23.11, 23.37, 25.24, 25.65, 26.01, 27.12, 28.32 degrees in term of two theta; In one embodiment, form B has an X-ray powder diffraction pattern comprising one or more peaks at about 5.79, 5.99, 11.54, 13.30, 14.68, 15.56, 16.31, 18.36, 20.07, 20.30, 20.66, 20.93, 21.08, 22.01, 22.40, 23.01, 23.11, 23.37, 25.24, 25.65, 26.01, 26.64, 27.12, 28.32, 29.53, 29.99, 32.98, 33.10, 36.48 degrees in term of two theta; In some embodiment, form B has an X-ray powder diffraction pattern substantially as depicted in FIG. 2 wherein the peak at about 23.11 degree in term of two theta has a relative intensity of at least about 50%, at least about 60%, at least about 70%, at least about 80%, at least about 90% or at least about 99% with respect to the strongest peak in the X-ray powder diffraction pattern.

In certain embodiments, the characteristics of form B can be detected, identified, classified and characterized using well-known techniques such as, but not limited to infrared (IR) spectroscopy, DSC, form B melts at about 211.4° C. to about 218.8° C. by DSC analysis.

In some embodiments, the crystalline form of azilsartan medoxomil potassium is crystalline form C. In certain embodiments, form C of azilsartan medoxomil potassium disclosed herein is substantially pure. In some embodiments, form C has an X-ray powder diffraction pattern (XRPD) comprising a peak at about 6.20 degree in term of two theta; In certain embodiment, form C has an X-ray powder diffraction pattern comprising one or more peaks at about 6.20, 18.70 degrees in term of two theta; In one embodiment, form C has an X-ray powder diffraction pattern comprising one or more peaks at about 6.20, 12.64, 13.36, 14.48, 16.00, 18.70, 20.30, 21.38, 22.78, 23.80, 25.04 degrees in term of two theta; In some embodiments, form C has an X-ray powder diffraction pattern comprising one or more peaks at about 6.20, 12.64, 13.36, 14.02, 14.48, 16.00, 17.74, 18.12, 18.70, 20.30, 21.38, 22.78, 23.80, 25.04, 25.60, 27.52, 28.16, 28.32, 31.32 degrees in term of two theta; In some embodiments, form C has an X-ray powder diffraction pattern substantially as depicted in FIG. 3 wherein the peak at about 6.20 degree in term of two theta has a relative intensity of at least about 50%, at least about 60%, at least about 70%, at least about 80%, at least about 90% or at least about 99% with respect to the strongest peak in the X-ray powder diffraction pattern.

Figure 4:
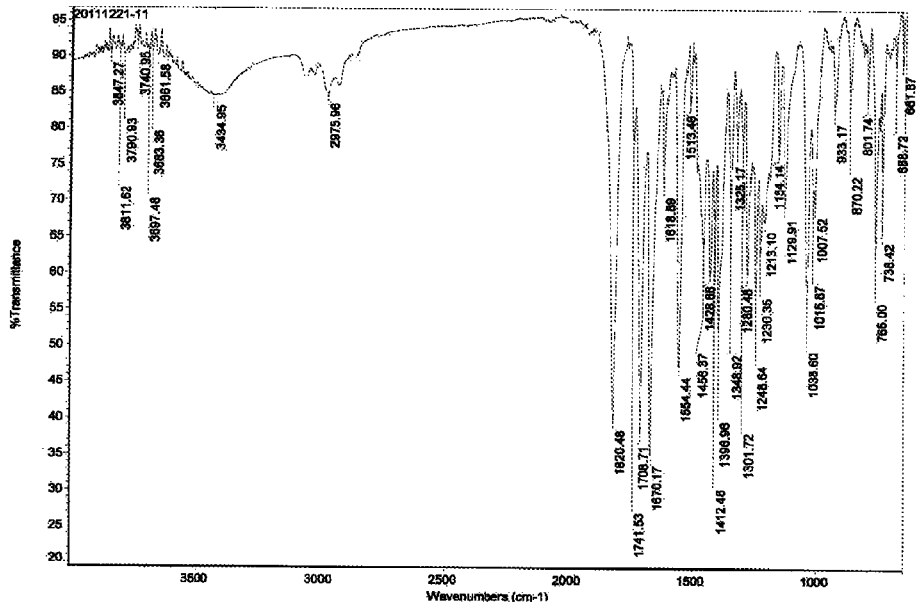
FIG. 4 depicts the infrared (IR) spectrum of the crystalline form C of azilsartan medoxomil potassium.

In certain embodiments, the characteristics of form C can be detected, identified, classified and characterized using well-known techniques such as, but not limited to IR, DSC, in one embodiment, form C melts at about 212.8° C. to about 223.8° C. by DSC analysis; in some embodiments, form C melts at about 221.4° C. to about 223.8° C. by DSC analysis; in one embodiment, form C melts at about 218.3° C. to about 223.0° C. by DSC analysis; in one embodiment, form C melts at about 214.7° C. to about 221.3° C. by DSC analysis; in some embodiments, form C melts at about 217.2° C. to about 222.3° C. by DSC analysis; in certain embodiments, the IR spectrum of form C is substantially as depicted in FIG. 4.

In some embodiments, the crystalline form of azilsartan medoxomil potassium is crystalline form D. In certain embodiments, form D of azilsartan medoxomil potassium disclosed herein is substantially pure. In some embodiments, form D has an X-ray powder diffraction pattern (XRPD) comprising a peak at about 6.18 degree in term of two theta;

In certain embodiment, form D has an X-ray powder diffraction pattern comprising one or more peaks at about 6.18, 18.62 degrees in term of two theta; In one embodiment, form D has an X-ray powder diffraction pattern comprising one or more peaks at about 6.18, 15.22, 18.62, 19.34, 23.54, 24.88, 26.94 degrees in term of two theta; In some embodiments, form D has an X-ray powder diffraction pattern comprising one or more peaks at about 6.18, 12.14, 12.90, 14.26, 14.84, 15.22, 18.62, 19.34, 20.16, 21.62, 23.54, 24.88, 26.94 degrees in term of two theta; In certain embodiment, form D has an X-ray powder diffraction pattern comprising one or more peaks at about 6.18, 12.14, 12.90, 13.64, 14.26, 14.84, 15.22, 17.38, 18.04, 18.62, 19.34, 20.16, 21.62, 22.30, 22.76, 23.54, 24.40, 24.88, 26.08, 26.94, 27.74, 31.56, 34.06; In some embodiments, form D has an X-ray powder diffraction pattern substantially as depicted in FIG. 5 wherein the peak at about 6.18 degree in term of two theta has a relative intensity of at least about 50%, at least about 60%, at least about 70%, at least about 80%, at least about 90% or at least about 99% with respect to the strongest peak in the X-ray powder diffraction pattern.

Figure 6:
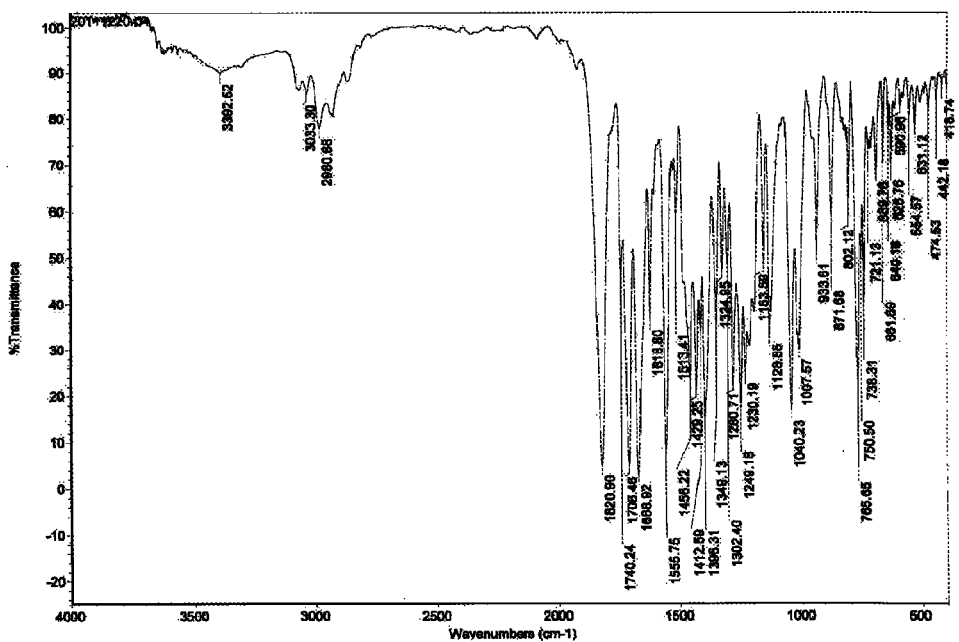
FIG. 6 depicts the infrared (IR) spectrum of the crystalline form D of azilsartan medoxomil potassium.

In certain embodiments, the characteristics of form D can be detected, identified, classified and characterized using well-known techniques such as, but not limited to IR, DSC, in one embodiment, form D melts at about 205.6° C. to about 220.1° C. by DSC analysis; in some embodiments, form D melts at about 206.6° C. to about 216.2° C. by DSC analysis; in one embodiment, form C melts at about 205.6° C. to about 216.7° C. by DSC analysis; in one embodiment, form D melts at about 214.8° C. to about 220.1° C. by DSC analysis; in one embodiment, form D melts at about 206.4° C. to about 214.3° C. by DSC analysis; in certain embodiments, the IR spectrum of form D is substantially as depicted in FIG. 6.

Figure 7:
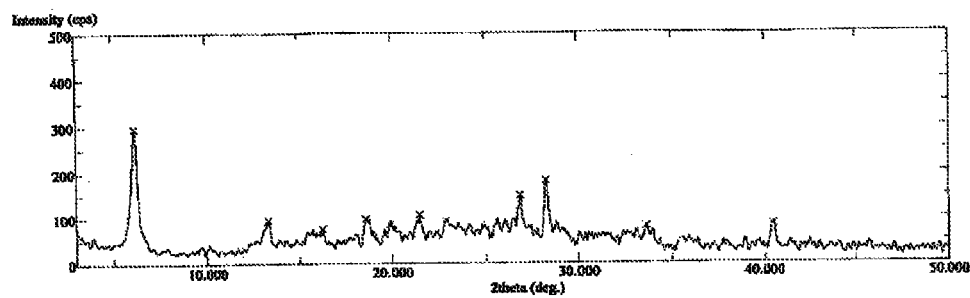
FIG. 7 depicts the X-ray powder diffractogram of the crystalline form E of azilsartan medoxomil potassium.

In some embodiments, the crystalline form of azilsartan medoxomil potassium is crystalline form E. In certain embodiments, form E of azilsartan medoxomil potassium disclosed herein is substantially pure. In some embodiments, form E has an X-ray powder diffraction pattern (XRPD) comprising a peak at about 6.16 degree in term of two theta; In certain embodiments, form E has an X-ray powder diffraction pattern comprising one or more peaks at about 6.16, 28.28 degrees in term of two theta; In some embodiments, form E has an X-ray powder diffraction pattern comprising one or more peaks at about 6.16, 13.34, 16.22, 18.58, 19.88, 21.46, 22.86, 26.84, 28.28, 33.62 degrees in term of two theta; In some embodiments, form E has an X-ray powder diffraction pattern substantially as depicted in FIG. 7 wherein the peak at about 6.16 degree in term of two theta has a relative intensity of at least about 50%, at least about 60%, at least about 70%, at least about 80%, at least about 90% or at least about 99% with respect to the strongest peak in the X-ray powder diffraction pattern.

Figure 8:
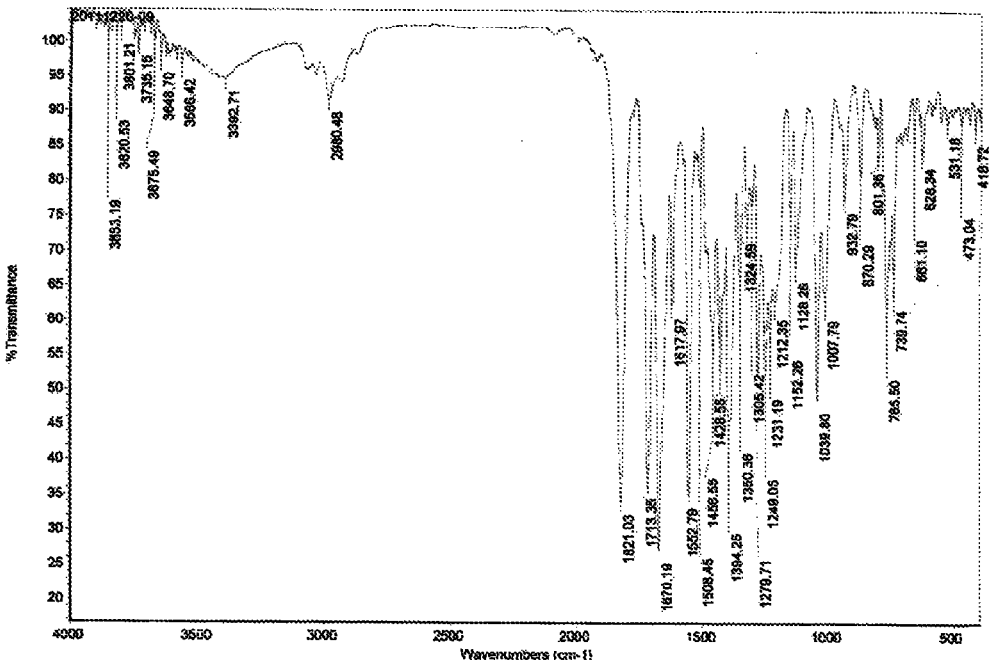
FIG. 8 depicts the infrared (IR) spectrum of the crystalline form E of azilsartan medoxomil potassium.

In certain embodiments, the characteristics of form E can be detected, identified, classified and characterized using well-known techniques such as, but not limited to IR, DSC, form E melts at about 198.3° C. to about 208.4° C. by DSC analysis, in certain embodiments, the IR spectrum of form E is substantially as depicted in FIG. 8.

In some embodiments, the crystalline form of azilsartan medoxomil potassium is crystalline form F. In certain embodiments, form F of azilsartan medoxomil potassium disclosed herein is substantially pure. In some embodiments, form F has an X-ray powder diffraction pattern (XRPD) comprising a peak at about 17.96, 22.52, 23.32 degree in term of two theta; In one embodiment, form F has an X-ray powder diffraction pattern comprising one or more peaks at about 5.90, 8.46, 17.26, 17.96, 19.60, 21.66, 22.52, 23.32 degrees in term of two theta; In certain embodiments, form F has an X-ray powder diffraction pattern substantially as depicted in FIG. 9.

Figure 10:
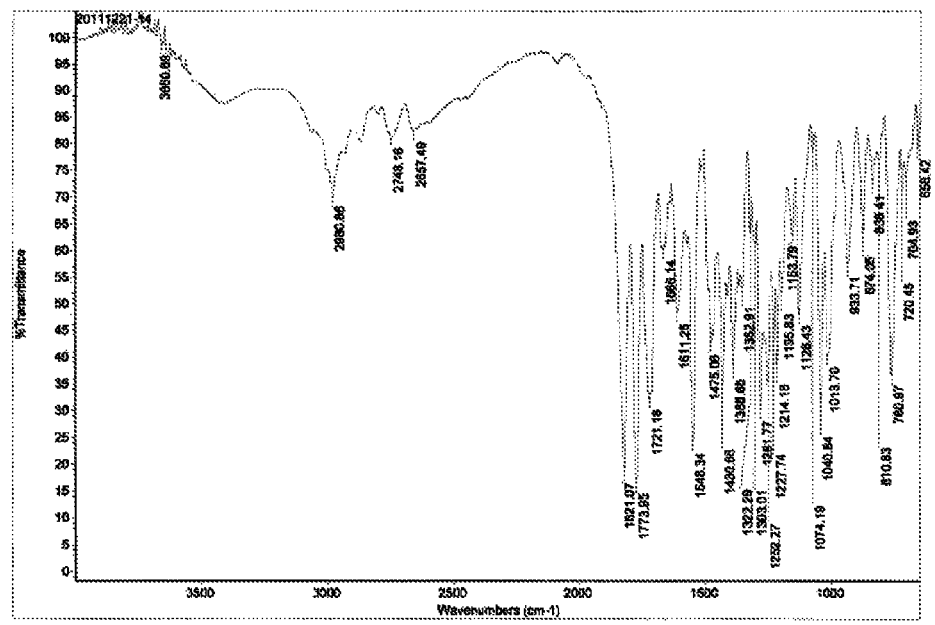
FIG. 10 depicts the infrared (IR) spectrum of the crystalline form F of azilsartan medoxomil potassium.

In certain embodiments, the characteristics of form F can be detected, identified, classified and characterized using well-known techniques such as, but not limited to IR, DSC, form F melts at about 94.2° C. to about 111.0° C. by DSC analysis; in certain embodiments, the IR spectrum of form D is substantially as depicted in FIG. 10.

Figure 11:
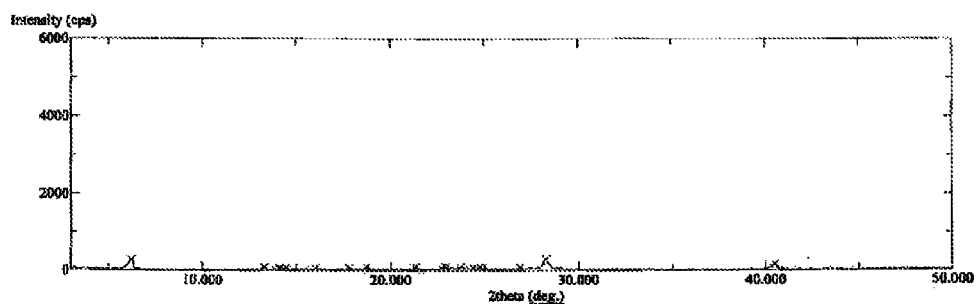
FIG. 11 depicts the X-ray powder diffractogram of the crystalline form G of azilsartan medoxomil potassium.

In some embodiments, the crystalline form of azilsartan medoxomil potassium is crystalline form G. In certain embodiments, form G of azilsartan medoxomil potassium disclosed herein is substantially pure. In some embodiments, form G has an X-ray powder diffraction pattern (XRPD) comprising a peak at about 28.28 degree in term of two theta; In some embodiments, form G has an X-ray powder diffraction pattern comprising one or more peaks at about 6.18, 28.28, 40.50 degrees in term of two theta; In certain embodiments, form G has an X-ray powder diffraction pattern comprising one or more peaks at about 6.18, 13.32, 14.10, 14.44, 16.02, 17.80, 18.70, 21.30, 22.70, 22.90, 23.70, 24.38, 24.74, 26.90, 28.28, 40.50 degrees in term of two theta; In some embodiments, form G has an X-ray powder diffraction pattern substantially as depicted in FIG. 11 wherein the peak at about 28.28 degree in term of two theta has a relative intensity of at least about 50%, at least about 60%, at least about 70%, at least about 80%, at least about 90% or at least about 99% with respect to the strongest peak in the X-ray powder diffraction pattern.

In certain embodiments, the characteristics of form G can be detected, identified, classified and characterized using well-known techniques such as, but not limited to IR, DSC.

In some embodiments, the crystalline form of azilsartan medoxomil potassium is crystalline form H. In certain embodiments, form H of azilsartan medoxomil potassium disclosed herein is substantially pure. In some embodiments, form H has an X-ray powder diffraction pattern (XRPD) comprising a peak at about 6.18 degree in term of two theta; In some embodiments, form H has an X-ray powder diffraction pattern comprising one or more peaks at about 6.18, 22.80 degrees in term of two theta; In certain embodiments, form H has an X-ray powder diffraction pattern comprising one or more peaks at about 6.18, 13.32, 14.10, 14.36, 17.34, 18.72, 22.80, 23.56, 27.02 degrees in term of two theta; In some embodiments, form H has an X-ray powder diffraction pattern comprising one or more peaks at about 6.18, 12.08, 13.32, 14.10, 14.36, 15.14, 15.92, 17.34, 18.02, 18.72, 19.24, 20.18, 21.68, 22.80, 23.56, 24.96, 27.02, 27.60, 30.2; In some embodiments, form H has an X-ray powder diffraction pattern substantially as depicted in FIG. 12 wherein the peak at about 6.18 degree in term of two theta has a relative intensity of at least about 50%, at least about 60%, at least about 70%, at least about 80%, at least about 90% or at least about 99% with respect to the strongest peak in the X-ray powder diffraction pattern.

In certain embodiments, the characteristics of form H can be detected, identified, classified and characterized using well-known techniques such as, but not limited to IR, DSC, form H melts at about 213° C. to about 218° C. by DSC analysis.

Figure 13:
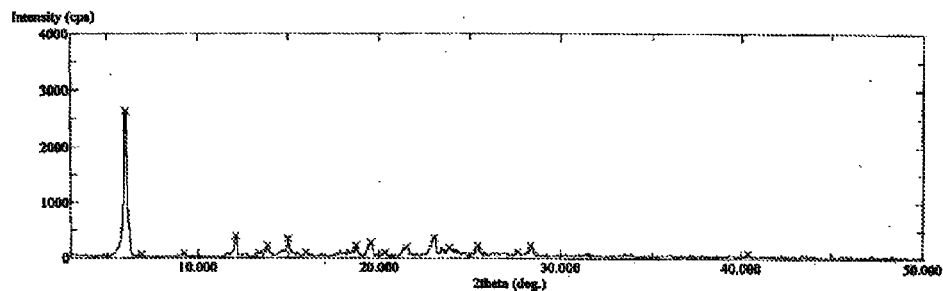
FIG. 13 depicts the X-ray powder diffractogram of the crystalline form I of azilsartan medoxomil potassium.

In some embodiments, the crystalline form of azilsartan medoxomil potassium is crystalline form I. In certain embodiments, form I of azilsartan medoxomil potassium disclosed herein is substantially pure. In some embodiments, form I has an X-ray powder diffraction pattern (XRPD) comprising a peak at about 6.06 degree in term of two theta; In some embodiments, form I has an X-ray powder diffraction pattern comprising one or more peaks at about 6.06, 12.10, 15.00, 19.54, 23.04 degrees in term of two theta; In certain embodiments, form I has an X-ray powder diffraction pattern comprising one or more peaks at about 6.06, 12.10, 13.86, 15.00, 18.72, 19.54, 21.54, 23.04, 23.88, 25.44, 28.36 degrees in term of two theta; In one embodiment, form I has an X-ray powder diffraction pattern substantially as depicted in FIG. 13 wherein the peak at about 6.06 degree in term of two theta has a relative intensity of at least about 50%, at least about 60%, at least about 70%, at least about 80%, at least about 90% or at least about 99% with respect to the strongest peak in the X-ray powder diffraction pattern.

In certain embodiments, the characteristics of form I can be detected, identified, classified and characterized using well-known techniques such as, but not limited to IR, DSC.

In some embodiments, the crystalline form of azilsartan medoxomil potassium is crystalline form J. In certain embodiments, form J of azilsartan medoxomil potassium disclosed herein is substantially pure. In some embodiments, form J has an X-ray powder diffraction pattern (XRPD) comprising a peak at about 13.18 degree in term of two theta; In some embodiments, form J has an X-ray powder diffraction pattern comprising one or more peaks at about 13.18, 23.24 degrees in term of two theta; In some embodiments, form J has an X-ray powder diffraction pattern comprising one or more peaks at about 13.18, 15.90, 20.18, 21.10, 22.22, 22.52, 23.24, 23.98 degrees in term of two theta; In certain embodiments, form J has an X-ray powder diffraction pattern comprising one or more peaks at about 5.94, 9.04, 9.94, 11.46, 11.88, 13.18, 14.26, 14.58, 15.90, 17.38, 17.80, 18.10, 19.32, 20.18, 21.10, 22.22, 22.52, 23.24, 23.98, 24.96, 26.44, 27.60, 28.30 degrees in term of two theta; In one embodiment, form J has an X-ray powder diffraction pattern substantially as depicted in FIG. 14 wherein the peak at about 13.18 degree in term of two theta has a relative intensity of at least about 50%, at least about 60%, at least about 70%, at least about 80%, at least about 90% or at least about 99% with respect to the strongest peak in the X-ray powder diffraction pattern.

In certain embodiments, the characteristics of form J can be detected, identified, classified and characterized using well-known techniques such as, but not limited to IR, DSC.

Figure 15:
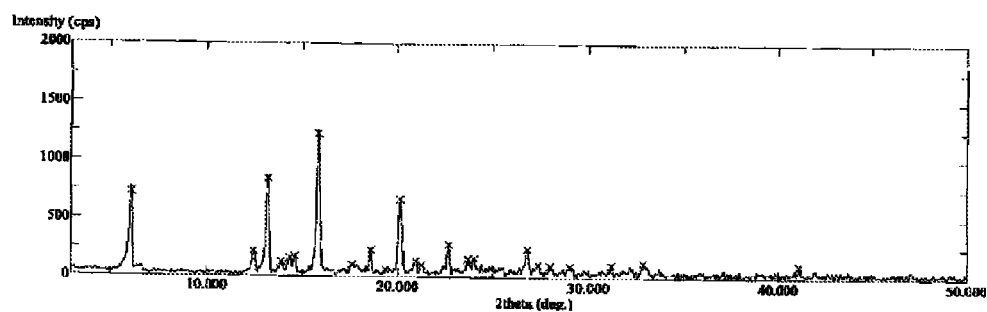
FIG. 15 depicts the X-ray powder diffractogram of the crystalline form K of azilsartan medoxomil potassium.

In some embodiments, the crystalline form of azilsartan medoxomil potassium is crystalline form K. In certain embodiments, form K of azilsartan medoxomil potassium disclosed herein is substantially pure. In some embodiments, form K has an X-ray powder diffraction pattern (XRPD) comprising a peak at about 15.84 degree in term of two theta; In certain embodiments, form K has an X-ray powder diffraction pattern comprising one or more peaks at about 6.06, 13.22, 15.84, 20.14 degrees in term of two theta; In some embodiments, form K has an X-ray powder diffraction pattern comprising one or more peaks at about 6.06, 12.48, 13.22, 13.92, 14.34, 14.62, 15.84, 18.60, 20.14, 20.92, 22.66, 23.66, 24.00, 26.86 degrees in term of two theta; In one embodiment, form K has an X-ray powder diffraction pattern comprising one or more peaks at about 6.06, 12.48, 13.22, 13.92, 14.34, 14.62, 15.84, 17.62, 18.60, 19.36, 20.14, 20.92, 21.24, 22.66, 23.66, 24.00, 26.86, 27.40, 28.06, 29.04, 31.20, 32.88 degrees in term of two theta; In some embodiments, form K has an X-ray powder diffraction pattern substantially as depicted in FIG. 15 wherein the peak at about 15.84 degree in term of two theta has a relative intensity of at least about 50%, at least about 60%, at least about 70%, at least about 80%, at least about 90% or at least about 99% with respect to the strongest peak in the X-ray powder diffraction pattern.

In certain embodiments, the characteristics of form K can be detected, identified, classified and characterized using well-known techniques such as, but not limited to IR, DSC.

In some embodiments, the crystalline form of azilsartan medoxomil potassium is crystalline form L. In certain embodiments, form L of azilsartan medoxomil potassium disclosed herein is substantially pure. In some embodiments, form L has an X-ray powder diffraction pattern (XRPD) comprising a peak at about 20.92 degree in term of two theta; In certain embodiments, form L has an X-ray powder diffraction pattern comprising one or more peaks at about 10.34, 18.26, 20.92, 22.10, 24.06 degrees in term of two theta; In one embodiment, form L has an X-ray powder diffraction pattern comprising one or more peaks at about 10.34, 10.82, 14.52, 15.52, 17.52, 18.26, 19.00, 20.54, 20.92, 21.38, 22.10, 22.84, 23.48, 24.06, 24.36, 25.56 degrees in term of two theta; In certain embodiments, form L has an X-ray powder diffraction pattern comprising one or more peaks at about 7.48, 10.34, 10.82, 12.04, 13.10, 14.52, 15.52, 16.88, 17.52, 18.26, 19.00, 19.62, 20.54, 20.92, 21.38, 22.10, 22.84, 23.48, 24.06, 24.36, 25.56, 26.36 degrees in term of two theta; In certain embodiments, form L has an X-ray powder diffraction pattern substantially as depicted in FIG. 16 wherein the peak at about 20.92 degree in term of two theta has a relative intensity of at least about 50%, at least about 60%, at least about 70%, at least about 80%, at least about 90% or at least about 99% with respect to the strongest peak in the X-ray powder diffraction pattern.

In certain embodiments, the characteristics of form L can be detected, identified, classified and characterized using well-known techniques such as, but not limited to IR, DSC.

According to the present invention, the X-ray powder diffraction was performed on the X-ray powder diffractometer model D/max-3A, data was collected over a 2 theta range of 3°-50°, scan rate 10°/min, using CuK.alpha radiation at a power of 25 mA and 35 kV. Wherein an ordinate or Y-axis is diffraction intensities in counts/second (cps) and an abscissa or X-axis is the diffraction angle two theta in degrees.

The IR spectrum was detected on iS10; DSC thermograms were collected on a TA/Q2000 instrument, the samples were analyzed under a flow of nitrogen at a scan rate of 10° C./minute, at Ramp 40-240° C.

It is worth noting that, for the X-ray powder diffraction peaks of a particular crystalline form, the two theta values may change slightly from one machine to another, from one sample to another. The difference in value may be about 1 degree, about 0.8 degrees, about 0.5 degrees, about 0.3 degrees, or about 0.1 degrees. Therefore, the above-mentioned values of two theta cannot be regarded as absolute.

The DSC thermograms may change slightly from one machine to another, and from one sample to another. The difference in value may be less than or equal to about 5° C., or less than or equal to about 4° C., or less than or equal to about 3° C., or less than or equal to about 2° C. Therefore, the melting points analysis by DSC given above cannot be regarded as absolute.

Also disclosed herein are two processes for preparing the crystalline forms A-L of azilsartan medoxomil potassium, wherein the processes comprise changing any one of the forms of azilsartan medoxomil potassium disclosed herein to another form of azilsartan medoxomil potassium. The crystalline forms of azilsartan medoxomil potassium salt obtained from the processes disclosed herein can be form A, form B, form C, form D, form E, form F, form G, form H, form I, form J, form K, and form L and wherein the novel crystalline form of azilsartan medoxomil potassium salt is substantially pure.

The first process for preparing the crystalline form of azilsartan medoxomil potassium salt disclosed herein comprising:
a) adding azilsartan medoxomil to a solvent to form a mixture;
b) heating the mixture or adding another solvent to form a solution;
c) adding a solution of the potassium salt to the solution;
d) forming crystals at a suitable temperature.

The azilsartan medoxomil can be prepared by using the process disclosed in U.S. Pat. No. 7,157,584.

The mixture may be heated to a temperature sufficient to obtain complete solution or partial solution. The mixture may be heated to a temperature from about 40° C. to the reflux temperature of the solution, or from about 55° C. to about 65° C. In some embodiments, the mixture may be heated to a temperature at about 60° C. In certain embodiments, the mixture may be heated to a reflux temperature.

The volume of solvent is from about 10 ml to about 300 ml per 1 g of azilsartan medoxomil. In some embodiments, the potassium salt is an organic acid potassium salt or an inorganic acid salt or a combination thereof. Some non-limiting examples of the inorganic acid salts include potassium nitrate, potassium sulfate, potassium sulfite, potassium bromate, potassium bicarbonate, potassium thiocyanate, dipotassium hydrogen phosphate, potassium dihydrogen phosphate and combinations thereof. Some non-limiting examples of the organic acid salts include potassium hydrogen phthalate, potassium acetate, potassium formate, potassium di-tert-butylphosphate, dipotassium glycyrrhizinate, potassium 2-ethylhexanoate, potassium ethyl xanthate, potassium sorbate and combinations thereof. The equivalent of potassium salt is from about 1.0 eq. to about 3.0 eq., or from about 1.0 eq. to about 2.0 eq., or from about 1.3 eq. to about 1.7 eq. with respect to azilsartan medoxomil.

The crystal was formed at a suitable temperature from about −20° C. to about 20° C., or from about 0° C. to about 10° C., or from about 0° C. to about 5° C.

The second process for preparing the crystalline form of azilsartan medoxomil potassium comprising: adding azilsartan medoxomil potassium salt to a solvent or a mixture of solvent at a suitable temperature to form a solution, if necessary, adding another solvent to promote forming the solution; and forming crystals by cooling the solution.

In some embodiments, the suitable temperature is about 40° C. to a reflux temperature, the solution was then cooled to a temperature from about −20° C. to about 10° C., or from about −10° C. to about 10° C., or from about 0° C. to about 5° C. In some embodiments, the crystal was formed by cooling the solution then adding an anti-solvent to the solution.

In some embodiments, the solvent for process 1 and process 2 disclosed herein comprises one or more polar solvents, one or more non-polar solvents or a combination thereof. In certain embodiments, the solvent is dimethyl formamide (DMF), dimethyl sulfoxide (DMSO), N-methyl-2-pyrrolidone (NMP), water, ether solvents, ketone solvents, ester solvents, aromatic hydrocarbon solvents, alkane solvents, nitrile solvents or combinations thereof. In other embodiments, the ether solvents are methyl tetrahydrofuran, tetrahydrofuran (THF), 1,4-dioxane, ethylene glycol dimethyl ether, methyl tert-butyl ether or a combination thereof. In some embodiments, the ketone solvents are acetone, butanone, or 4-methyl-2-pentanone or a combination thereof. In some embodiments the ester solvents are ethyl acetate, isopropyl acetate, n-butyl acetate, tert-butyl acetate, sec-butyl acetate or a combination thereof; In some embodiments the hydrocarbon solvents are n-hexane, cyclohexane or n-pentane or n-heptane, toluene, xylene or a combination thereof; In some embodiments, halogenated solvents are dichloromethane (DCM), 1,2-dichloroethane, chloroform, carbon tetrachloride or a combination thereof; In some embodiments, nitrile solvents are acetonitrile (MeCN) or malononitrile or a combination thereof; In some embodiments, the nitro solvents are nitroethane, nitromethane, nitrobenzene or a combination thereof Provided herein is a process for preparing the crystalline form A of azilsartan medoxomil potassium salt comprising: adding azilsartan medoxomil to acetone; heating to reflux to form a solution; adding a solution of the potassium salt in acetone to the solution; then addition of acetic acid to attain a pH of 5-6, forming crystals at a suitable temperature.

Provided herein is a process for preparing the crystalline form B of azilsartan medoxomil potassium salt comprising: adding azilsartan medoxomil to acetone; heating to reflux to form a solution; adding a solution of the potassium salt in acetone to the solution; forming crystals at a suitable temperature.

The process disclosed herein for preparing crystalline form C of azilsartan medoxomil potassium is substantially pure, wherein the solvent is propanone, 4-methyl-2-pentanone, ethyl acetate, dichloromethane, dichloroethane, iso-butyl acetate, sec-butyl acetate, methyl tetrahydrofuran, nitroethane, 1,2-dichloroethane, methyl ethyl ketone, 1,4-dioxane, ethylene glycol dimethyl ether, acetonitrile, tetrahydrofuran, cyclohexane or a combination thereof. In some embodiments, the solvent is a mixture of acetone and 1,4-dioxane, or a mixture of ethylene glycol dimethyl ether and acetonitrile, or a mixture of acetone and tetrahydrofuran, or a mixture of acetone and acetonitrile, or a mixture of acetone and sec-butyl acetate, or a mixture of tetrahydrofuran and dichloroethane, or a mixture of tetrahydrofuran and cyclohexane, or a mixture of acetone and dichloroethane, or a mixture of acetone and cyclohexane.

The process for preparing crystalline form D of azilsartan medoxomil potassium in substantially pure, wherein the solvent is selected from 1,4-dioxane, ethylene glycol dimethyl ether, acetonitrile, DMSO, acetone and combinations thereof. In some embodiment, the solvent is a mixed solvent of DMSO and acetone.

Also provided herein is a process for preparing crystalline form E of azilsartan medoxomil potassium, wherein the solvent is chloroform.

Also provided herein is a process for preparing crystalline form F of azilsartan medoxomil potassium, wherein the solvent is tert-butyl acetate or DMF and combinations thereof.

Also provided herein is a process for preparing crystalline form G of azilsartan medoxomil potassium, wherein the solvent is THF or carbon tetrachloride and combinations thereof.

Also provided herein is a process for preparing crystalline form H of azilsartan medoxomil potassium, wherein the solvent is ethylene glycol dimethylether, DMF, toluene, ethyl acetate, 1,4-dioxane, sec-butyl acetate or combinations thereof. In some embodiments, the solvent is a mixed solvent of ethylene glycol dimethyl ether, and DMF, or a mixed solvent of toluene and 1,4-dioxane, or a mixed solvent of ethyl acetate and 1,4-dioxane, or a mixed solvent of 1,4-dioxane and sec-butyl acetate.

Also provided herein is a process for preparing crystalline form I of azilsartan medoxomil potassium, wherein the solvent is acetonitrile or acetone and combinations thereof.

Also provided herein is a process for preparing crystalline form J of azilsartan medoxomil potassium, wherein the solvent is acetone, water, ethylene glycol dimethyl ether, tetrahydrofuran, DMSO, dichloromethane, acetonitrile, N-methyl pyrrolidone and combinations thereof. In some embodiments, the solvent is a mixed solvent of acetone and water; In some embodiments, the solvent is a mixed solvent of ethylene glycol dimethyl ether and tetrahydrofuran, or a mixed solvent of DMSO and dichloromethane, or a mixed solvent of acetone, ethylene glycol dimethyl ether and water, or a mixed solvent of acetonitrile and water, or a mixed solvent of acetonitrile, N-methylpyrrolidone and water.

Also provided herein is a process for preparing crystalline form K of azilsartan medoxomil potassium, wherein the solvent is acetonitrile.

Also provided herein is a process for preparing crystalline form L of azilsartan medoxomil potassium, wherein the solvent is tetrahydrofuran, water, NMP, DMF or 1,4-dioxane and combinations thereof. In some embodiments, the solvent is a mixed solvent of tetrahydrofuran and water, or a mixed solvent of tetrahydrofuran and NMP, or a mixed solvent of DMF and 1,4-dioxane.

The novel crystalline forms of azilsartan medoxomil potassium disclosed herein generally have good properties such as high solubility; thermal stability; better oral bioavailability; better dissolution profile for particular formulations; free-flowing; easily filterable; thermally stable which is suitable for particular formulations. The novel crystalline forms of azilsartan medoxomil potassium disclosed herein generally have good antistatic property which is convenient for operating the production process. The novel crystalline forms of azilsartan medoxomil potassium generally exhibit an excellent performance in reducing clinical systolic blood pressure (SBP) and average 24-hour SBP. Therefore novel crystalline forms of azilsartan medoxomil potassium can be used for preparing a pharmaceutical composition for the prevention or treatment of hypertension.

In illustrative embodiments of the present invention, novel crystalline form A, form B, form C, form D, form E, form F, form G, form H, form I, form J, form K, form L of azilsartan medoxomil potassium is substantially pure, wherein the process for preparing the novel crystalline forms generally complies with the factory GMP production requirements, and is suitable for industrial production.

Also provided herein is a pharmaceutical composition comprising a therapeutically effective amount of a novel crystalline form disclosed herein such as form A, form B, form C, form D, form E, form F, form G, form H, form I, form J, form K, form L of azilsartan medoxomil potassium and one or more pharmaceutically acceptable carriers, excipients or diluents.

In certain embodiments, the pharmaceutical composition comprises crystalline forms of azilsartan medoxomil potassium, wherein the pharmaceutical compositions that are compacted into a dosage form, such as tablets, pills, powders and granules. The pharmaceutical compositions may include excipients or carriers, wherein the excipients or carriers comprise sodium citrate, calcium phosphate, fillers, binders, moisturizers, disintegrants, retarders, absorption enhancer, wetting agents, absorbents, lubricants and a combination thereof, wherein the fillers include starch, lactose, sucrose, glucose, mannitol, silicic acid and a combination thereof, wherein the binders include carboxymethylcellulose, alginates, gelatin, polyvinylpyrrolidone, sucrose, gum Arabic and a combination thereof, wherein the moisturizers include glycerol, wherein the disintegrants include agar-agar, calcium carbonate, potato starch or tapioca starch, alginic acid, certain silicates, and sodium carbonate, low substituted hydroxypropyl cellulose and a combination thereof; wherein the blockers solution include paraffin; wherein the absorption enhancer include quaternary ammonium compounds; wherein the wetting agents include cetyl alcohol, monostearic acid glyceride and a combination thereof; wherein the absorbents include kaolin, bentonite and a combination thereof; wherein the lubricants include talc, calcium stearate, magnesium stearate, solid polyethylene glycols, sodium lauryl sulfate and a combination thereof.

The crystalline form of azilsartan medoxomil potassium disclosed herein or the pharmaceutical composition disclosed herein can be used in preventing or treating hypertension in a patient.

Also provided herein is a method of preventing or treating hypertension in a patient by administering to the patient a pharmaceutically effective amount of the crystalline form of azilsartan medoxomil potassium disclosed herein or the pharmaceutical composition disclosed herein.

Also provided herein is use of a pharmaceutical composition comprising a therapeutically effective amount of form A, form B, form C, form D, form E, form F, form G, form H, form I, form J, form K, form L of azilsartan medoxomil potassium and one or more pharmaceutically acceptable carriers, excipients or diluents to treat conditions in a subject in need thereof, such as a strong and long lasting angiotensin II antagonistic activity and hypotensive action, and an insulin sensitizing activity, and circulatory diseases such as hypertension, cardiac diseases (e.g. cardiac hypertrophy, cardiac failure, cardiac infarction).

EXAMPLES

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range.

Example 1

Preparation of Crystalline Form A of Azilsartan Medoxomil Potassium

Azilsartan medoxomil (1.0 g) was dissolved in acetone (20 mL) at a reflux temperature to form a solution, the solution was cooled to 50° C., a solution of potassium 2-ethyl hexanoate (0.35 g) in acetone (1 mL) was added slowly to the solution, the solution was slowly lowered to 0° C., followed by addition of acetic acid drop-wise to attain a pH of 5-6, stirred for 5 hours at 0° C. and filtered, the solid was dried under vacuum at 45° C. for 12 hours to obtain white powder, the white powder was found to be crystalline form A of azilsartan medoxomil potassium having an XRPD as depicted in FIG. 1.

Example 2

Preparation of Crystalline Form B of Azilsartan Medoxomil Potassium

Azilsartan medoxomil (1.0 g) was dissolved in acetone (20 mL) at a reflux temperature to form a solution, after the solution was cooled to 50° C., a solution of potassium 2-ethyl hexanoate (0.35 g) in acetone (1 mL) was added, the solution was slowly lowered to 0° C., further stirred for 5 hours at 0°

C. and filtered, the solid was found to be crystalline form B of azilsartan medoxomil potassium having an XRPD as depicted in FIG. 2.

Example 3 to example 25 were the preparation of crystalline form C of azilsartan medoxomil potassium

Example 3

Azilsartan medoxomil (1.0 g) was dissolved in acetone (20 mL) at a reflux temperature to form a solution, after the solution was cooled to 50° C., was added a solution of potassium 2-ethyl hexanoate (0.35 g) in acetone (1 mL), the solution was slowly lowered to 0° C. and stirred for 5 hours at 0° C., then precipitated out, filtered, the solid was dried under vacuum at 45° C. for 12 hours to obtain white powder, the white powder was found to be crystalline form C of azilsartan medoxomil potassium having an XRPD as depicted in FIG. 3.

Example 4

Azilsartan medoxomil (1.0 g) was dissolved in THF (20 mL) at a reflux temperature to form a solution, after the solution was cooled to 50° C., a solution of potassium 2-ethyl hexanoate (0.5 g) in THF (2 mL) was added slowly to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 5

Azilsartan medoxomil (1.0 g) was dissolved in 4-methyl-2-pentanone (80 mL) at a reflux temperature to form a solution, after the solution was cooled to 50° C., a solution of potassium 2-ethyl hexanoate (0.5 g) in 4-methyl-2-pentanone (2 mL) was added slowly to the solution to form a reaction mixture, the reaction mixture was slowly lowered to 0° C., further stirred for 5 hours at 0° C., the crystal was collected by filtration, dried under vacuum at 45° C. for 12 hours to obtain white powder, XRPD indicated that it was form C of azilsartan medoxomil potassium.

Example 6

Azilsartan medoxomil (1.0 g) was dissolved in ethyl acetate (80 ml) at 60° C. to form a solution, after the solution was cooled to 50° C., a solution of potassium 2-ethyl hexanoate (0.5 g) in ethyl acetate (2 mL) was added slowly to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 7

Azilsartan medoxomil (1.0 g) was dissolved in acetone (80 ml) at 60° C. to form a solution, after the solution was cooled to 50° C., a solution of potassium 2-ethyl hexanoate (0.5 g) in acetone (2 mL) was added slowly to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 8

Azilsartan medoxomil (1.0 g) was dissolved in DCM (100 ml) at 60° C. to form a solution, after the solution was cooled to 50° C., a solution of potassium 2-ethyl hexanoate (0.5 g) in acetone (2 mL) was added slowly to the solution to form a reaction mixture, the reaction mixture was slowly lowered to 0° C., stirred for 5 hours at 0° C., the crystal was collected by filtration, dried under vacuum at 45° C. for 12 hours to obtain a white powder, XRPD indicated that the white powder was form C of azilsartan medoxomil potassium.

Example 9

Azilsartan medoxomil (1.0 g) was dissolved in isobutyl acetate (90 ml) at 60° C. to form a solution, after the solution was cooled to 50° C., a solution of potassium 2-ethyl hexanoate (0.5 g) in isobutyl acetate (2 mL) was added slowly to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that the white powder was form C of azilsartan medoxomil potassium.

Example 10

Azilsartan medoxomil (1.0 g) was dissolved in sec-butyl acetate (200 ml) at 60° C. to form a solution, after the solution was cooled to 50° C., a solution of potassium 2-ethyl hexanoate (0.5 g) in sec-butyl acetate (2 mL) was added slowly to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that the white powder was form C of azilsartan medoxomil potassium.

Example 11

Azilsartan medoxomil (1.0 g) was dissolved in 2-methyltetrahydrofuran (90 ml) at 60° C. to form a solution, after the solution was cooled to 50° C., a solution of potassium 2-ethyl hexanoate (0.5 g) in 2-methyltetrahydrofuran (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that the white powder was form C of azilsartan medoxomil potassium.

Example 12

Azilsartan medoxomil (1.0 g) was dissolved in nitroethane (130 ml) at 60° C. to form a solution, after the solution was cooled to 50° C., a solution of potassium 2-ethyl hexanoate (0.5 g) in iso-butyl acetate (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that the white powder was form C of azilsartan medoxomil potassium.

Example 13

Azilsartan medoxomil (1.0 g) was dissolved in 1,2-dichloroethane (90 ml) at 60° C. to form a solution, after the solution was cooled to 50° C., a solution of potassium 2-ethyl hexanoate (0.5 g) in acetone (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 14

Azilsartan medoxomil (1.0 g) was dissolved in butanone (25 ml) at 60° C. to form a solution, after the solution was cooled to 50° C., a solution of potassium 2-ethyl hexanoate (0.5 g) in butanone (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 15

Azilsartan medoxomil (1.0 g) was added to sec-butyl acetate (15 ml) at 60° C. to form a mixture, to the mixture was added acetone (20 ml) to form a solution, the solution was cooled to 50° C., a solution of potassium 2-ethyl hexanoate (0.5 g) in acetone (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 16

Azilsartan medoxomil (1.0 g) was added to 1,2-dichloroethane (15 ml) at 60° C. to form a mixture, to the mixture was added THF (15 ml) to form a solution, the solution was cooled to 50° C., a solution of potassium 2-ethyl hexanoate (0.5 g) in acetone (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 17

Azilsartan medoxomil (1.0 g) was added to cyclohexane (20 ml) at 60° C. to form a mixture, to the mixture was added THF (30 ml) to form a solution, the solution was cooled to 50° C., a solution of potassium 2-ethyl hexanoate (0.5 g) in THF (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 18

Azilsartan medoxomil (1.0 g) was added to 1,2-dichloroethane (15 ml) at 60° C. to form a mixture, to the mixture was added acetone (15 ml) to form a solution, after the solution was cooled to 50° C., a solution of potassium 2-ethyl hexanoate (0.5 g) in acetone (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 19

Azilsartan medoxomil (1.0 g) was added to cyclohexane (20 ml) at 60° C. to form a mixture, to the mixture was added acetone (25 ml) to form a solution, after the solution was cooled to 50° C., a solution of potassium 2-ethyl hexanoate (0.5 g) in acetone (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 20

Azilsartan medoxomil (1.0 g) was added to a mixed solvent of 1,4-dioxane (15 ml) and acetone (15 ml) at 60° C. to form a solution, after the solution was cooled to 50° C., a solution of potassium 2-ethyl hexanoate (0.5 g) in acetone (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 21

Azilsartan medoxomil (1.0 g) was added to acetonitrile (15 ml) at 60° C. to form a mixture, to the mixture was added ethylene glycol dimethyl ether (15 ml) to form a solution, after the solution was cooled to 50° C., a solution of potassium 2-ethyl hexanoate (0.5 g) in ethylene glycol dimethyl ether (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 22

Azilsartan medoxomil (1.0 g) was added to a mixed solvent of acetone (15 ml) and THF (10 ml) at 60° C. to form a solution, after the solution was cooled to 50° C., a solution of potassium 2-ethyl hexanoate (0.5 g) in acetone (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 23

Azilsartan medoxomil (1.0 g) was added to acetonitrile (10 ml) at 60° C. to form a mixture, to the mixture was added acetone (15 ml) to form a solution, after the solution was cooled to 50° C., a solution of potassium 2-ethyl hexanoate (0.5 g) in acetone (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder, XRPD indicated that it was form C of azilsartan medoxomil potassium.

Example 24

Azilsartan medoxomil potassium (1.0 g) was added to acetone (300 ml), heating to reflux to form a solution, the solution was slowly lowered to 0° C., further stirred for 5 hours at 0° C., the crystal was collected by filtration, dried under vacuum at 45° C. for 12 hours to obtain white powder, XRPD indicated that it was form C of azilsartan medoxomil potassium.

Example 25

Azilsartan medoxomil potassium (1.0 g) was added to acetonitrile (200 ml) at 60° C. to form a solution, the solution was slowly lowered to 0° C., stirred at 0° C. for 5 hours, the crystal was collected by filtration, dried under vacuum at 45° C. for 12 hours to obtain white powder, XRPD indicated that it was form C of azilsartan medoxomil potassium.

Example 26

Preparation of Crystalline Form D of Azilsartan Medoxomil Potassium

Azilsartan medoxomil (1.0 g) was dissolved in 1,4-dioxane (20 ml) at 60° C. to form a solution, after the solution was cooled to 50° C., a solution of potassium 2-ethyl hexanoate (0.5 g) in 1,4-dioxane (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder which was found to be crystalline form D of azilsartan medoxomil potassium having an XRPD as depicted in FIG. 5.

Example 27

Preparation of Crystalline Form D of Azilsartan Medoxomil Potassium

Azilsartan medoxomil (1.0 g) was dissolved in ethylene glycol dimethyl ether (35 ml) at 60° C. to form a solution, after the solution was cooled to 50° C., a solution of potassium 2-ethyl hexanoate (0.5 g) in ethylene glycol dimethyl ether (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder which was found to be crystalline form D of azilsartan medoxomil potassium having an XRPD as depicted in FIG. 5.

Example 28

Preparation of Crystalline Form D of Azilsartan Medoxomil Potassium

Azilsartan medoxomil potassium (1.0 g) was added to acetone (60 ml) at to form a mixture, to the mixture was added DMSO (3 ml) to form a solution, the solution was slowly lowered to 0° C., stirred for 5 hours at 0° C., the crystal was collected by filtration, dried under vacuum at 45° C. for 12 hours to obtain white powder, XRPD indicated that it was form D of azilsartan medoxomil potassium.

Example 29

Preparation of Crystalline Form E of Azilsartan Medoxomil Potassium

Azilsartan medoxomil (1.0 g) was dissolved in chloroform (85 ml) at 60° C. to form a solution, after the solution was cooled to 50° C., a solution of potassium 2-ethyl hexanoate (0.5 g) in acetone (2 mL) was added to the solution to form a reaction mixture, the reaction mixture was slowly lowered to 0° C., further stirred for 5 hours at 0° C., the crystal was collected by filtration, dried under vacuum at 45° C. for 12 hours to obtain white powder which was found to be crystalline form E of azilsartan medoxomil potassium having an XRPD as depicted in FIG. 7.

Example 30

Preparation of Crystalline Form F of Azilsartan Medoxomil Potassium

Azilsartan medoxomil (1.0 g) was dissolved in tert-butyl acetate (200 ml) at 60° C. to form a solution, after the solution was cooled to 50° C., a solution of potassium 2-ethyl hexanoate (0.5 g) in tert-butyl acetate (2 mL) was added to the solution to form a reaction mixture, the reaction mixture was slowly lowered to 0° C., stirred for 5 hours at 0° C., the crystal was collected by filtration, dried under vacuum at 45° C. for 12 hours to obtain white powder which was found to be crystalline form F of azilsartan medoxomil potassium having an XRPD as depicted in FIG. 9.

Example 31

Preparation of Crystalline Form F of Azilsartan Medoxomil Potassium

Azilsartan medoxomil potassium (1.0 g) was added to tert-butyl acetate (60 ml) at 60° C. to form a mixture, to the mixture was added DMF (3 ml) to form a solution, the solution was slowly lowered to 0° C., followed by added water (100 ml), then precipitation out a white solid, further stirred for 5 hours at 0° C., the solid was collected by filtration, dried under vacuum at 45° C. for 12 hours to obtain white powder, XRPD indicated that it was form F of azilsartan medoxomil potassium Example 32

Preparation of Crystalline Form G of Azilsartan Medoxomil Potassium

Azilsartan medoxomil (1.0 g) was added to tetrachloromethane (15 ml) at 60° C. to form a mixture, to the mixture was added THF (18 ml) to form a solution, after the solution was cooled to 50° C., a solution of potassium 2-ethyl hexanoate (0.5 g) in THF (2 mL) was added to the solution to form a reaction mixture which was slowly lowered to 0° C., stirred for 5 hours at 0° C., the crystal was collected by filtration, dried under vacuum at 45° C. for 12 hours to obtain white powder, XRPD indicated that it was form G of azilsartan medoxomil potassium.

Example 33

Preparation of Crystalline Form H of Azilsartan Medoxomil Potassium

Azilsartan medoxomil (1.0 g) was added to toluene (15 ml) at to form a mixture, to the mixture was added 1,4-dioxane (30 ml) to form a solution, after the solution was cooled to 50° C., a solution of potassium 2-ethyl hexanoate (0.5 g) in 1,4- dioxane (2 mL) was added to the solution to form a reaction mixture which was slowly lowered to 0° C., further stirred for 5 hours at 0° C., the crystal was collected by filtration, dried under vacuum at 45° C. for 12 hours to obtain white powder, XRPD indicated that it was form H of azilsartan medoxomil potassium.

Example 34

Preparation of Crystalline Form H of Azilsartan Medoxomil Potassium

Azilsartan medoxomil (1.0 g) was added to ethyl acetate (15 ml) at to form a mixture, to the mixture was added 1,4-dioxane (20 ml) to form a solution, after the solution was cooled to 50° C., a solution of potassium 2-ethyl hexanoate (0.5 g) in 1,4-dioxane (2 mL) was added to the solution to form a reaction mixture which was slowly lowered to 0° C., further stirred for 5 hours at 0° C., the crystal was collected by filtration, dried under vacuum at 45° C. for 12 hours to obtain white powder, XRPD indicated that it was form H of azilsartan medoxomil potassium.

Example 35

Preparation of Crystalline Form H of Azilsartan Medoxomil Potassium

Azilsartan medoxomil (1.0 g) was added to sec-butyl acetate (15 ml) at to form a mixture, to the mixture was added 1,4-dioxane (15 ml) to form a solution, after the solution was cooled to 50° C., a solution of potassium 2-ethyl hexanoate (0.5 g) in 1,4-dioxane (2 mL) was added to the solution to form a reaction mixture which was slowly lowered to 0° C., further stirred for 5 hours at 0° C., the crystal was collected by filtration, dried under vacuum at 45° C. for 12 hours to obtain white powder, XRPD indicated that it was form H of azilsartan medoxomil potassium.

Example 36

Preparation of Crystalline Form H of Azilsartan Medoxomil Potassium

Azilsartan medoxomil potassium (1.0 g) was added to ethylene glycol dimethyl ether (40 ml) at to form a mixture, to the mixture was added DMF (10 ml) to form a solution, after the solution was cooled to 20° C., crystalline out, the mixture was further stirred for 5 hours at 20° C., the crystal was collected by filtration, dried under vacuum at 45° C. for 12 hours to obtain white powder, XRPD indicated that it was form H of azilsartan medoxomil potassium.

Example 37

Preparation of Crystalline Form I of Azilsartan Medoxomil Potassium

Azilsartan medoxomil (1.0 g) was dissolved in acetonitrile (90 ml) at 60° C. to form a solution, after the solution was cooled to 50° C., a solution of potassium 2-ethyl hexanoate (0.5 g) in acetone (2 mL) was added to the solution to form a reaction mixture, the reaction mixture was slowly lowered to 0° C., further stirred for 5 hours at 0° C., the crystal was collected by filtration, dried under vacuum at 45° C. for 12 hours to obtain white powder which was found to be crystalline form I of azilsartan medoxomil potassium having an XRPD as depicted in FIG. 13.

Example 38

Preparation of Crystalline Form J of Azilsartan Medoxomil Potassium

Azilsartan medoxomil potassium (1.0 g) was added to acetone (40 ml) at to form a mixture, to the mixture was added water (1 ml) to form a solution, the solution was cooled to 50° C., to the solution was added water (100 ml) to form a mixture, the mixture was slowly lowered to 0° C., keeping stirring for 5 hours at 0° C., the crystal was collected by filtration, dried under vacuum at 45° C. for 12 hours to obtain white powder, XRPD indicated that it was form J of azilsartan medoxomil potassium.

Example 39

Preparation of Crystalline Form J of Azilsartan Medoxomil Potassium

Azilsartan medoxomil (1.0 g) was added to a mixed solvent of ethylene glycol dimethyl ether (15 ml) and THF (15 ml) at 60° C. to form a solution, after the solution was cooled to 50° C., a solution of potassium 2-ethyl hexanoate (0.5 g) in THF (2 mL) was added to the solution to form a reaction mixture, the reaction mixture was slowly lowered to 0° C., further stirred for 5 hours at 0° C., the crystal was collected by filtration, dried under vacuum at 45° C. for 12 hours to obtain white powder which was found to be crystalline form J of azilsartan medoxomil potassium having an XRPD as depicted in FIG. 14.

Example 40

Preparation of Crystalline Form J of Azilsartan Medoxomil Potassium

Azilsartan medoxomil potassium (1.0 g) was added to DCM (60 ml) at 60° C. to form a mixture, to the mixture was added DMSO (4 ml) to form a solution, the solution was slowly lowered to 0° C., further stirred for 5 hours at 0° C., the crystal was collected by filtration, dried under vacuum at 45° C. for 12 hours to obtain white powder, XRPD indicated that it was form J of azilsartan medoxomil potassium.

Example 41

Preparation of Crystalline Form J of Azilsartan Medoxomil Potassium

Azilsartan medoxomil potassium (1.0 g) was added to acetone (40 ml) at 60° C. to form a mixture, to the mixture was added a mixed solvent of ethylene glycol dimethyl ether (20 ml) and water (4 ml) to form a solution, the solution was slowly lowered to 0° C., further stirred for 5 hours at 0° C., the crystal was collected by filtration, dried under vacuum at 45° C. for 12 hours to obtain white powder, XRPD indicated that it was form J of azilsartan medoxomil potassium.

Example 42

Preparation of Crystalline Form J of Azilsartan Medoxomil Potassium

Azilsartan medoxomil potassium (1.0 g) was added to acetonitrile (40 ml) at 60° C. to form a mixture, to the mixture was added water (1 ml) to form a solution, after the solution was slowly lowered to 0° C., was added water (60 ml), the above mixture was further stirred for 5 hours at 0° C., the crystal was collected by filtration, dried under vacuum at 45°

C. for 12 hours to obtain white powder, XRPD indicated that it was form J of azilsartan medoxomil potassium.

Example 43

Preparation of Crystalline Form J of Azilsartan Medoxomil Potassium

Azilsartan medoxomil potassium (1.0 g) was added to acetonitrile (40 ml) at 60° C. to form a mixture, to the mixture was added NMP (20 ml) to form a solution, the solution was cooled to 0° C., followed by added water (120 ml) which was further stirred for 5 hours at 0° C., the crystal was collected by filtration, dried under vacuum at 45° C. for 12 hours to obtain white powder, XRPD indicated that it was form J of azilsartan medoxomil potassium.

Example 44

Preparation of Crystalline Form K of Azilsartan Medoxomil Potassium

Azilsartan medoxomil potassium (1.0 g) was added to acetonitrile (100 ml) at 60° C. to form a solution, the solution was slowly lowered to 0° C., then was further stirred for 5 hours at 0° C., the crystal was collected by filtration, dried under vacuum at 45° C. for 12 hours to obtain white powder, XRPD indicated that it was form K of azilsartan medoxomil potassium.

Example 45

Preparation of Crystalline Form L of Azilsartan Medoxomil Potassium

Azilsartan medoxomil potassium (1.0 g) was added to THF (20 ml) at to form a mixture, to the mixture was added water (1 ml) to form a solution, the solution was cooled to 50° C., followed by added water (150 ml) which was slowly lowered to 0° C. and stirred for 5 hours at 0° C., the crystal was collected by filtration, dried under vacuum at 45° C. for 12 hours to obtain white powder, XRPD indicated that it was form L of azilsartan medoxomil potassium.

Example 46

Preparation of Crystalline Form L of Azilsartan Medoxomil Potassium

Azilsartan medoxomil potassium (1.0 g) was added to THF (60 ml) at 60° C. to form a mixture, to the mixture was added NMP (3 ml) to form a solution, after the solution was slowly cooled to 0° C., was added water (100 ml), then crystalline out, the mixture was further stirred for 5 hours at 0° C., the crystal was collected by filtration, dried under vacuum at 45° C. for 12 hours to obtain white powder, XRPD indicated that it was form L of azilsartan medoxomil potassium.

Example 47

Preparation of Crystalline Form L of Azilsartan Medoxomil Potassium

Azilsartan medoxomil potassium (1.0 g) was added to 1,4-dioxane (50 ml) at to form a mixture, to the mixture was added DMF (10 ml) to form a solution, the solution was cooled to 0° C. and was added water (50 ml) to form a mixture, the mixture was further stirred for 5 hours at 0° C., the crystal was collected by filtration, dried under vacuum at 45° C. for 12 hours to obtain white powder, XRPD indicated that it was form L of azilsartan medoxomil potassium.

Example 48

Preparation of Crystalline Form L of Azilsartan Medoxomil Potassium

Azilsartan medoxomil potassium (1.0 g) was added to THF (40 ml) at to form a mixture, to the mixture was added a mixed solvent of ethylene glycol dimethyl ether (20 ml) and water (1 ml) to form a solution, after the solution was slowly cooled to 0° C., was added water (100 ml) which was further stirred for 5 hours at 0° C., the crystal was collected by filtration, dried under vacuum at 45° C. for 12 hours to obtain white powder, XRPD indicated that it was form L of azilsartan medoxomil potassium.

Example 49

Stability Test

The stability test of the crystalline form C was conducted under the following conditions:

Storage condition 1: stored under conditions of 40° C./RH75% in a sealed state for 3 and 6 months. As a result, conversion of the crystalline form C into other polymorphs could not be confirmed after six months under the storage condition 1. During the whole test period, no change in total amount of impurities was recognized as compared with that before the beginning of the test.

Storage condition 2: stored under conditions of 40° C./RH75% in an unsealed state for 1 and 3 months.

As a result, conversion of the crystalline form C into other polymorphs could not be confirmed after three months under the storage condition 2 but the total amount of impurities increased as compared with that before the beginning of the test.

Example 50

Solubility Test

The crystalline form C, D, F, H, J and L of azilsartan medoxomil potassium (0.50 g) was added to the solvent at room temperature. The solid was dissolved by shaking for 30 seconds every 5 minutes and then the solubility of the solid was observed with eyes. The solid was deemed as dissolved when no solid was detected in the mixture by human eyes.

The solubility data of crystalline forms C, D, F, H, J and L of azilsartan medoxomil potassium are as shown below.

|  | Methanol | Ethanol | Acetone | THF | Ethyl acetate | Result |
|---|---|---|---|---|---|---|
| Form C | 5 ml | 6 ml | 8 ml | 13 ml | 10 ml | dissolved |
| Form D | 4 ml | 5 ml | 9 ml | 16.5 ml | 12 ml | dissolved |
| Form F | 4.5 ml | 6 ml | 12 ml | 15 ml | 16 ml | dissolved |
| Form H | 6 ml | 8 ml | 10 ml | 14 ml | 13 ml | dissolved |
| Form J | 4 ml | 5.5 ml | 8 ml | 12 ml | 11 ml | dissolved |
| Form L | 5 ml | 6 ml | 11 ml | 17 ml | 14 ml | dissolved |

Example 51

A tablet contains crystalline form A of azilsartan medoxomil potassium, comprising: crystalline form A of azilsartan medoxomil potassium, mannitol, fumaric acid, sodium hydroxide, hydroxypropyl cellulose, crosslinked cellulose, microcrystalline cellulose, magnesium stearate.

Example 52

A tablet contains crystalline form B of azilsartan medoxomil potassium, comprising: crystalline form B of azilsartan medoxomil potassium, mannitol, fumaric acid, sodium hydroxide, hydroxypropyl cellulose, crosslinked cellulose, microcrystalline cellulose, magnesium stearate.

Example 53

A tablet contains crystalline form C of azilsartan medoxomil potassium comprising: crystalline form C of azilsartan medoxomil potassium, mannitol, fumaric acid, sodium hydroxide, hydroxypropyl cellulose, crosslinked cellulose, microcrystalline cellulose, magnesium stearate.

Example 54

A tablet contains crystalline form D of azilsartan medoxomil potassium comprising: crystalline form D of azilsartan medoxomil potassium, mannitol, fumaric acid, sodium hydroxide, hydroxypropyl cellulose, crosslinked cellulose, microcrystalline cellulose, magnesium stearate.

Example 55

A tablet contains crystalline form H of azilsartan medoxomil potassium, comprising: crystalline form H of azilsartan medoxomil potassium, mannitol, fumaric acid, sodium hydroxide, hydroxypropyl cellulose, crosslinked cellulose, microcrystalline cellulose, magnesium stearate.

Example 56

A tablet contains crystalline form L of azilsartan medoxomil potassium, comprising: crystalline form L of azilsartan medoxomil potassium, mannitol, fumaric acid, sodium hydroxide, hydroxypropyl cellulose, crosslinked cellulose, microcrystalline cellulose, magnesium stearate.

The invention claimed is:

1. A crystalline form of azilsartan medoxomil potassium, wherein the crystalline form is form A, form B, form C, form D, form E, form F, form G, form H, form I, form J, form K or form L and wherein:
   a) form A has an X-ray powder diffraction pattern comprising peaks at 7.41, 10.74, 18.19, 22.83, 23.29, 23.66 and 24.80 degrees +/−5% in term of two theta;
   b) form B has an X-ray powder diffraction pattern comprising peaks at 23.01, 23.11, 26.01, and 28.32 degrees +/−5% in term of two theta;
   c) form C has an X-ray powder diffraction pattern comprising peaks at 6.20 and 18.70 degrees +/−5% in term of two theta;
   d) form D has an X-ray powder diffraction pattern comprising peaks at 6.18, 15.22, 18.62, 19.34, 23.54, 24.88, and 26.94 degrees +/−5% in term of two theta;
   e) form E has an X-ray powder diffraction pattern comprising peaks at 6.16, 13.34, 16.22, 18.58, 19.88, 21.46, 22.86, 26.84, 28.28, and 33.62 degrees +/−5% in term of two theta;
   f) form F has an X-ray powder diffraction pattern comprising peaks at 17.96, 22.52, and 23.32 degrees +/−5% in term of two theta;
   g) form G has an X-ray powder diffraction pattern comprising peaks at 6.18, 13.32, 14.10, 14.44, 16.02, 17.80, 18.70, 21.30, 22.70, 22.90, 23.70, 24.38, 24.74, 26.90, 28.28, and 40.50 degrees +/−5% in term of two theta;
   h) form H has an X-ray powder diffraction pattern comprising peaks at 6.18, 13.32, 14.10, 14.36, 17.34, 18.72, 22.80, 23.56, and 27.02 degrees +/−5% in term of two theta;
   i) form I has an X-ray powder diffraction pattern comprising peaks at 6.06, 12.10, 13.86, 15.00, 18.72, 19.54, 21.54, 23.04, 23.88, 25.44, and 28.36 degrees +/−5% in term of two theta;
   j) form J has an X-ray powder diffraction pattern comprising peaks at 13.18, 15.90, 20.18, 21.10, 22.22, 22.52, 23.24, and 23.98 degrees +/−5% in term of two theta;
   k) form K has an X-ray powder diffraction pattern comprising peaks at 6.06, 12.48, 13.22, 13.92, 14.34, 14.62, 15.84, 18.60, 20.14, 20.92, 22.66, 23.66, 24.00, and 26.86 degrees +/−5% in term of two theta; or
   l) form L has an X-ray powder diffraction pattern comprising peaks at 10.34, 18.26, 20.92, 22.10, and 24.06 degrees +/−5% in term of two theta.

2. The crystalline form of azilsartan medoxomil potassium of claim 1, wherein the crystalline form is form C, wherein form C has an X-ray powder diffraction pattern comprising peaks at 6.20, 12.64, 13.36, 14.48, 16.00, 18.70, 20.30, 21.38, 22.78, 23.80, and 25.04 degrees +/−5% in term of two theta.

3. The crystalline form of azilsartan medoxomil potassium of claim 1, wherein the crystalline form is form D, wherein form D has an X-ray powder diffraction pattern comprising peaks at 6.18, 12.14, 12.90, 14.26, 14.84, 15.22, 18.62, 19.34, 20.16, 21.62, 23.54, 24.88, and 26.94 degrees +/−5% in term of two theta.

4. The crystalline form of azilsartan medoxomil potassium of claim 1, wherein the crystalline form is form F, wherein form F has an X-ray powder diffraction pattern comprising peaks at 5.90, 8.46, 17.26, 17.96, 19.60, 21.66, 22.52, and 23.32 degrees +/−5% in term of two theta.

5. The crystalline form of azilsartan medoxomil potassium of claim 1, wherein the crystalline form is form H, wherein form H has an X-ray powder diffraction pattern comprising peaks at 6.18, 12.08, 13.32, 14.10, 14.36, 15.14, 15.92, 17.34, 18.02, 18.72, 19.24, 20.18, 21.68, 22.80, 23.56, 24.96, 27.02, 27.60, and 30.2 degrees +/−5% in term of two theta.

6. The crystalline form of azilsartan medoxomil potassium of claim 1, wherein the crystalline form is form J, wherein form J has an X-ray powder diffraction pattern comprising peaks at 5.94, 9.04, 9.94, 11.46, 11.88, 13.18, 14.26, 14.58, 15.90, 17.38, 17.80, 18.10, 19.32, 20.18, 21.10, 22.22, 22.52, 23.24, 23.98, 24.96, 26.44, 27.60, and 28.30 degrees +/−5% in term of two theta.

7. The crystalline form of azilsartan medoxomil potassium of claim 1, wherein the crystalline form is form L, wherein form L has an X-ray powder diffraction pattern comprising peaks at 10.34, 10.82, 14.52, 15.52, 17.52, 18.26, 19.00, 20.54, 20.92, 21.38, 22.10, 22.84, 23.48, 24.06, 24.36, and 25.56 degrees +/−5% in term of two theta.

8. A pharmaceutical composition comprising the crystalline form of azilsartan medoxomil potassium of claim 1 and one or more of inert excipients or carriers.

9. The composition of claim 8, wherein the crystalline form of azilsartan medoxomil potassium is form A, form B, form C, form D, form E, form F, form G, form H, form I, form J, form K or form L and wherein said crystalline form of azilsartan medoxomil potassium is substantially pure.

10. A method of treating hypertension in a patient by administering to the patient a pharmaceutically effective amount of the crystalline form of azilsartan medoxomil potassium of claim.

11. The crystalline form of azilsartan medoxomil potassium of claim 1, wherein the crystalline form is form C, wherein form C has an X-ray powder diffraction pattern comprising peaks at 6.20, 12.64, 13.36, 14.02, 14.48, 16.00, 17.74, 18.12, 18.70, 20.30, 21.38, 22.78, 23.80, 25.04, 25.60, 27.52, 28.16, 28.32, and 31.32 degrees +/−5% in term of two theta.

12. The crystalline form of azilsartan medoxomil potassium of claim 1, wherein the crystalline form is form C, wherein form C has an X-ray powder diffraction pattern substantially as depicted in FIG. 3 wherein the peak at 6.20 degree +/−5% in term of two theta has a relative intensity of at least about 50% with respect to the strongest peak in the X-ray powder diffraction pattern.

13. The crystalline form of azilsartan medoxomil potassium of claim 1, wherein the crystalline form is form C, wherein form C has an X-ray powder diffraction pattern substantially as depicted in FIG. 3 wherein the peak at 6.20 degree +/−5% in term of two theta has a relative intensity of at least about 70% with respect to the strongest peak in the X-ray powder diffraction pattern.

14. The crystalline form of azilsartan medoxomil potassium of claim 1, wherein the crystalline form is form C, wherein form C has an X-ray powder diffraction pattern substantially as depicted in FIG. 3 wherein the peak at 6.20 degree +/−5% in term of two theta has a relative intensity of at least about 90% with respect to the strongest peak in the X-ray powder diffraction pattern.

* * * * *